(12) United States Patent
Cussonneau et al.

(10) Patent No.: US 11,797,897 B2
(45) Date of Patent: Oct. 24, 2023

(54) PLACEMENT OF PHYSICO-CHEMICAL PARAMETER SENSORS IN A FLUID

(71) Applicant: SUEZ INTERNATIONAL, Paris la Defense (FR)

(72) Inventors: Guillaume Cussonneau, Paris (FR); Gilles Fay, Paris (FR); Zdravka Do Quang, Bailly (FR); Jean-Marc Lier, Pessac (FR); Jean-François Renard, Palaiseau (FR); Aurélie Chazerain, Paris (FR)

(73) Assignee: SUEZ INTERNATIONAL, la Défense (FR)

( * ) Notice: Subject to any disclaimer, the term of this patent is extended or adjusted under 35 U.S.C. 154(b) by 382 days.

(21) Appl. No.: 17/258,739

(22) PCT Filed: Jul. 8, 2019

(86) PCT No.: PCT/EP2019/068254
§ 371 (c)(1),
(2) Date: Jan. 7, 2021

(87) PCT Pub. No.: WO2020/011711
PCT Pub. Date: Jan. 16, 2020

(65) Prior Publication Data
US 2021/0272028 A1   Sep. 2, 2021

Related U.S. Application Data

(60) Provisional application No. 62/695,370, filed on Jul. 9, 2018.

(30) Foreign Application Priority Data

Oct. 10, 2018 (FR) .................................. 1859402

(51) Int. Cl.
*G06Q 10/04* (2023.01)
*G06Q 50/06* (2012.01)
(Continued)

(52) U.S. Cl.
CPC .......... *G06Q 10/043* (2013.01); *G06Q 50/06* (2013.01); *E03B 7/07* (2013.01); *F17D 3/01* (2013.01)

(58) Field of Classification Search
CPC ......... G06Q 50/06; G06Q 10/043; E03B 7/07
(Continued)

(56) References Cited

U.S. PATENT DOCUMENTS 9,964,468 B1 * 5/2018 Wu .................... G01M 5/00
10,161,749 B1 * 12/2018 Wu .................... G06F 30/18
(Continued)

FOREIGN PATENT DOCUMENTS

| EP | 3 112 960 A1 | 1/2017 |
|---|---|---|
| WO | 2018/001627 A1 | 1/2018 |
| WO | 2019/063648 A1 | 4/2019 |

OTHER PUBLICATIONS

Lechgar, et al., "Artificial Intelligence (AI) Contribution to GIS in Optimal Positioning of Hydrophone Sensors Using Genetic Algorithm (Case Study: Water Network, Casablanca, Morocco)", Proceedings of the Mediterranean Conference on Information & Communication Technologies 2015, pp. 11-19, 2015.
(Continued)

*Primary Examiner* — Ricky Go
(74) *Attorney, Agent, or Firm* — BakerHostetler

(57) ABSTRACT

A method is provided for placing sensors in a fluid distribution network by simulating network operating scenarios; by determining candidate sets of sensor positions; by determining the measurements of each sensor in each scenario, and the detection of associated anomalies; by attributing a
(Continued)

score to each candidate set of sensor positions, representing the capacity of the sensors placed in the positions of the set to accomplish a mission. Finally, the candidate sets are modified using so-called genetic algorithms until a stop criterion is validated. The genetic algorithms can for example consist in crossing over or mutating candidate sets.

17 Claims, 10 Drawing Sheets

(51) Int. Cl.
  *E03B 7/07* (2006.01)
  *F17D 3/01* (2006.01)
(58) Field of Classification Search
  USPC .......................................................... 702/50
  See application file for complete search history.

(56) References Cited

U.S. PATENT DOCUMENTS

| | | | |
|---|---|---|---|
| 11,250,177 B2* | 2/2022 | Schumacher | G06F 30/18 |
| 2013/0262068 A1* | 10/2013 | Israeli | F17D 5/02 |
| | | | 703/9 |
| 2013/0332090 A1* | 12/2013 | Scolnicov | G01F 1/74 |
| | | | 702/50 |
| 2014/0163916 A1* | 6/2014 | Ba | G06F 30/13 |
| | | | 702/100 |
| 2020/0264151 A1 | 8/2020 | Do Quang et al. | |

OTHER PUBLICATIONS

Cheifetz, et al., "A greedy algorithm for the positioning of quality sensors in a large water distribution network", Techniques Sciences Méthodes, (11), pp. 55-63, Nov. 1, 2017.

* cited by examiner

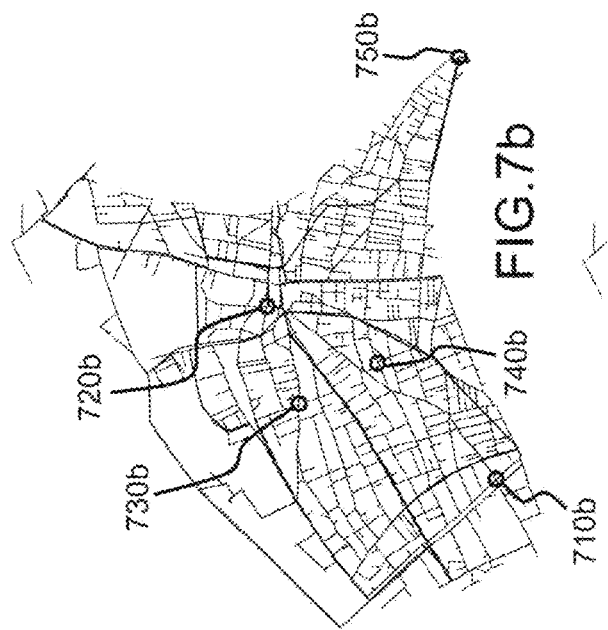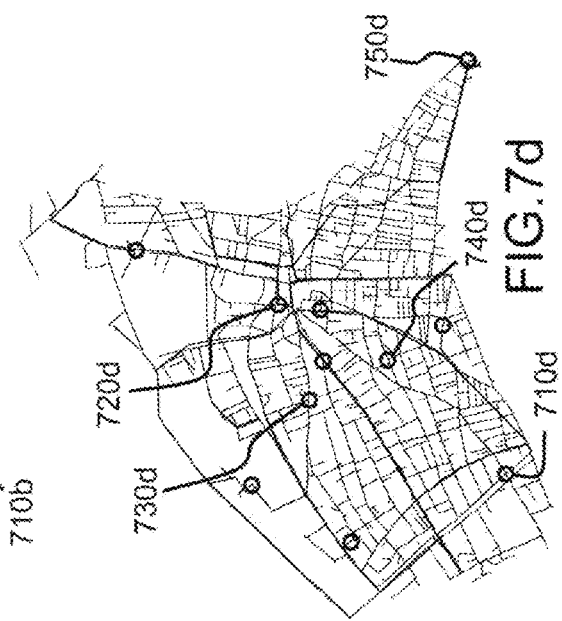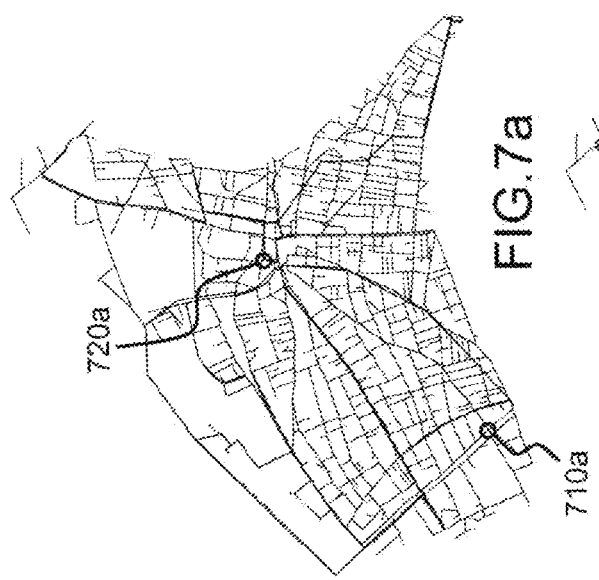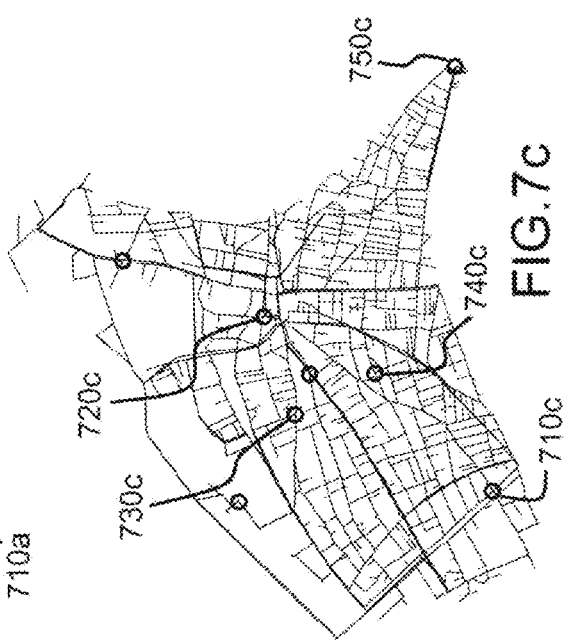

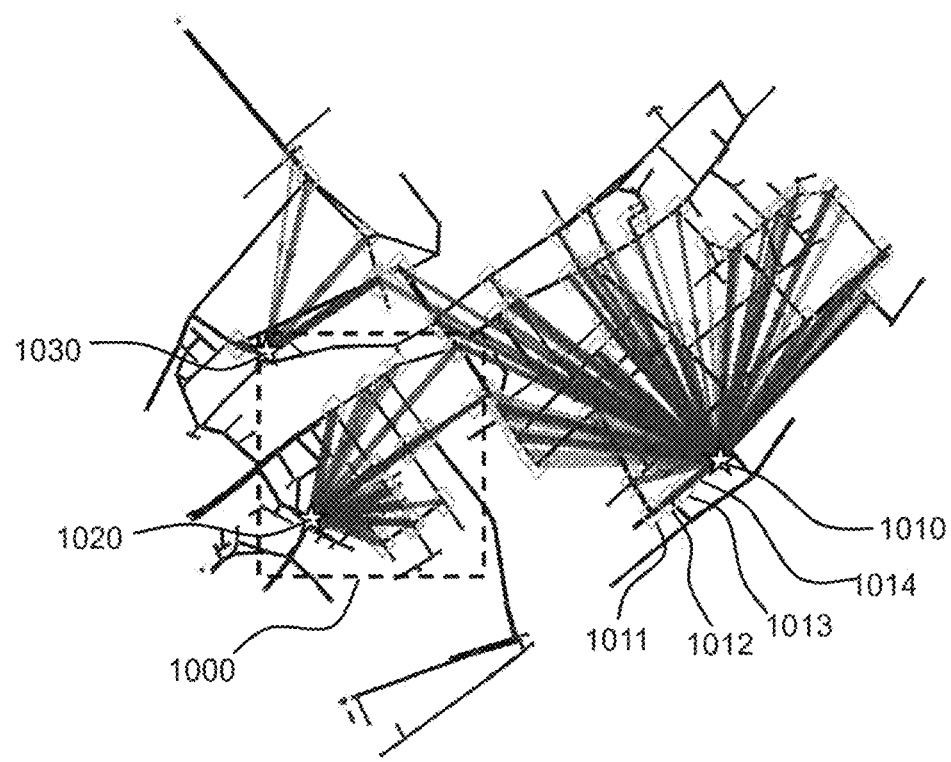
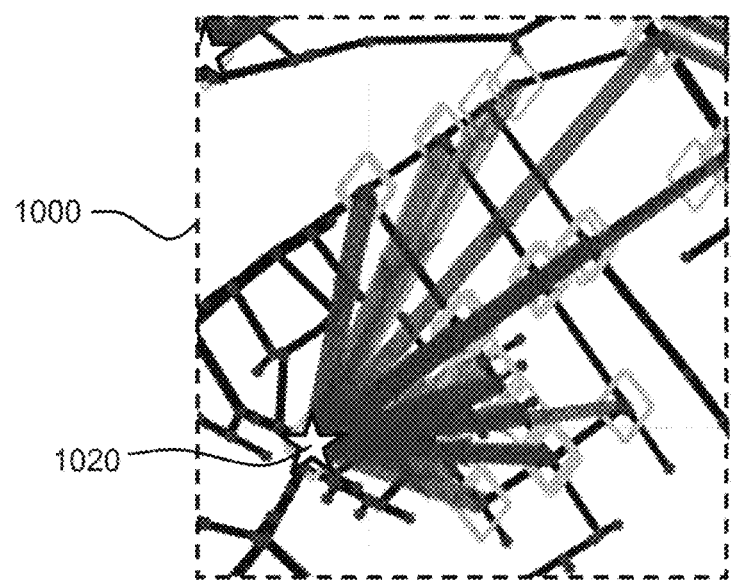
FIG.10

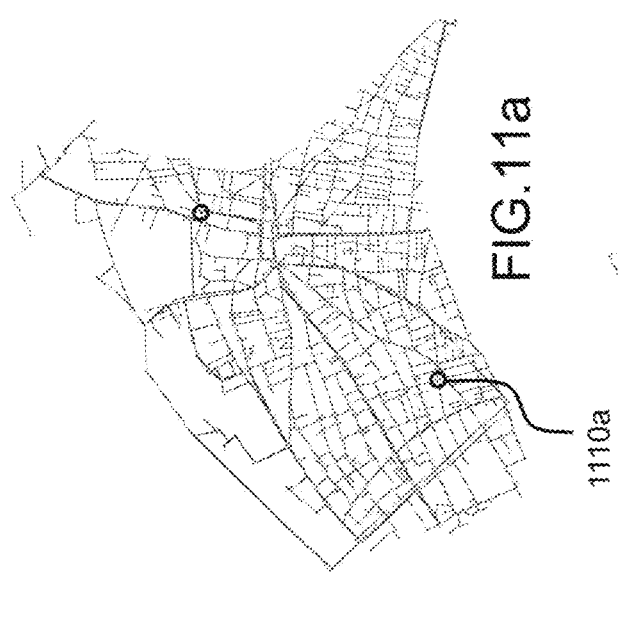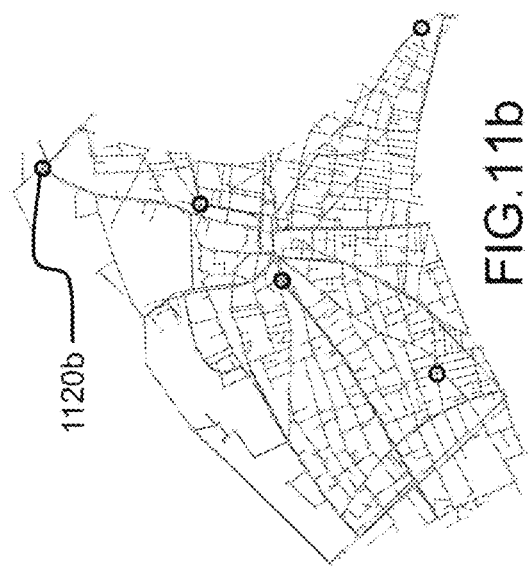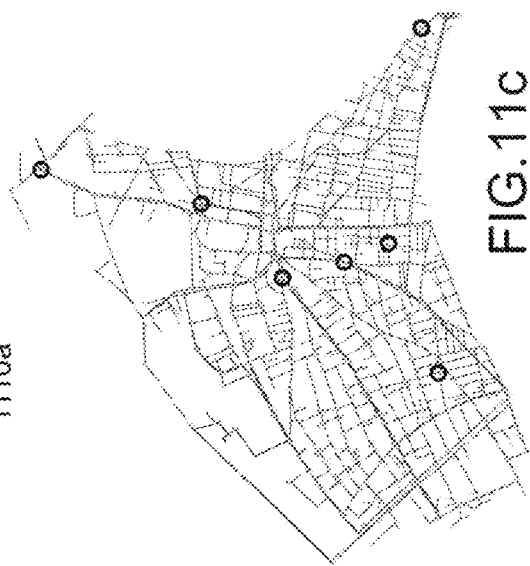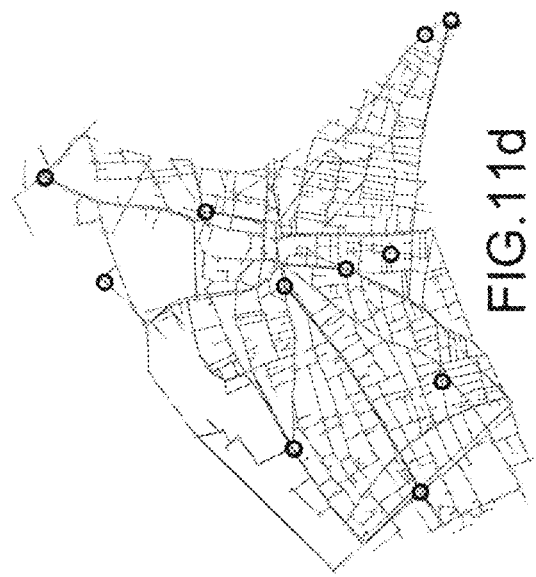

PLACEMENT OF PHYSICO-CHEMICAL PARAMETER SENSORS IN A FLUID

CROSS-REFERENCE TO RELATED APPLICATIONS

This application is a National Stage of International patent application PCT/EP2019/068254, filed on Jul. 8, 2019, which claims priority to U.S. Provisional Patent Application No. 62/695,370 filed Jul. 9, 2018, and to foreign French patent application No. FR 1859402, filed on Oct. 10, 2018, the disclosures of which are incorporated by reference in their entireties.

FIELD OF THE INVENTION

The present invention relates to the field of fluid distribution networks, such as water or gas distribution networks. More particularly, the present invention relates to the determination of optimized positions of sensors allowing measurement of the physicochemical fluid data.

BACKGROUND

Water distribution networks can be affected by numerous anomalies affecting the quality of the water. For example, the water can be contaminated by various pollutants introduced deliberately (malicious act) or accidentally by backflow or connection error, by particles of substances that are deposited regularly in the pipes and suddenly returned to suspension, by the reaction with the constituent materials of the networks, or by bacteria upon bacterial regrowth phenomena. In order to prevent the damaging effects that can be caused by the contamination, or more generally by the reduction of the quality of the water that can result in discomfort among the users (change of color, taste, smell, etc.), it is important to detect and characterize, as rapidly and accurately as possible, any event affecting the quality of the water. Problems affecting the quality of the water can also occur in natural water systems, expanses or courses such as lakes, ponds or rivers or sets of natural water expanses and courses. These systems can be affected for example by accidental pollutions, or the abnormal growth of algae, significantly degrading their condition and preventing their use (potabilization, bathing waters, etc.).

The water distribution networks can also see other anomalies occur such as leaks, excessively high pressures or excessively low pressures, badly positioned valves, etc. Other fluid distribution networks, such as gas distribution networks, or oil pipeline networks, can be affected by anomalies, for example overpressures or leaks, requiring corrective actions.

With the use of connected sensors, the effectiveness of the detection of anomalies in fluid distribution networks has been able to be considerably increased. Such sensors allow one or more physicochemical parameters (pressure, velocity, turbidity, pH, etc.) of the fluid to be measured at a point of the network, and these parameter values to be locally analyzed, or transmitted to a server for analysis. Thus, anomalies or pollutions of a fluid distribution network can be detected automatically, and the corrective or preventive actions can be put in place immediately. The French patent application no 1763286, filed by the applicant of this present application, describes a device for detecting anomalies in a water continuum based on measurements of physicochemical parameters in the water continuum.

Anomalies in a fluid distribution network can appear at various points of the network. For example, a pollution in a water distribution network can appear in a reservoir at the point of entry to the network, but also at another point of the network, for example an industrial plant in which a backflow might be triggered. A pollution created in this way can, by its nature, be detected only when an abnormal variation of parameters has been able to be detected by at least one sensor, that is to say when the pollution has arrived at that sensor. An undetected pollution is extremely problematic, particularly for potable water distribution networks, for which it can affect the health of the users of the network. It can also cause a problem without affecting the health of the users and generally requires curative and harmful actions for the continuity of the service.

The detection of the anomalies can be improved by increasing the number of sensors in the water distribution network. However, these sensors are expensive to purchase and use, notably because of their maintenance. It is therefore important to allow for an anomaly detection that is as rapid as possible, for the greatest possible part of a water distribution network, with the smallest possible number of sensors. A suitable arrangement of the sensors is therefore essential, to achieve a satisfactory detection of anomalies with a limited number of sensors.

The problem of optimal placement of a given number of sensors in a water distribution network is an extremely complex combinatorial problem. It is in practice impossible to test all of the solutions on a water distribution network of standard size (for example on the scale of a town or of a region), because an exhaustive testing of all the possible combinations of sensor positions requires computation capabilities that are too great to be implemented in practice.

Cheifetz, N., Sandraz, A. C., Feliers, C., Gilbert, D., Piller, O., & Heim, V. (2017). A greedy algorithm for the positioning of quality sensors in a large water distribution network. *Techniques Sciences Méthodes*, (11), 55-63. propose placing sensors in a water distribution network using a so-called "greedy" algorithm, that is to say by placing, iteratively, a given number of sensors one by one, at a position considered to be optimal in combination with the sensors already placed. While it allows a fairly satisfactory sensor placement to be obtained using limited computation capabilities, this algorithm does not generally allow an optimal placement of the sensors to be obtained. Indeed, once a sensor is placed, its position can no longer be questioned, even though that position, considered optimal based on the positions of the sensors previously placed, would no longer be so with a greater number of sensors.

There is therefore a need for a method that allows for an optimal placement of a given number of sensors in a water distribution network, in order to detect an anomaly in the water distribution network as soon as possible, regardless of the source of the anomaly.

There is, more generally, the need for a method allowing for an optimal placement of a given number of sensors in a fluid distribution network, in order to optimize the detection of anomalies in the fluid.

SUMMARY OF THE INVENTION

The invention achieves this aim by simulating scenarios that introduce, for at least some, anomalies into the fluid; by determining candidate sets of sensors positions; by determining the simulated values of the parameters of the fluid at each position and in each scenario, and the associated anomaly detection; by attributing a score to each candidate set of sensor positions, representing the effectiveness with which the sensors, placed at the positions of each candidate set, have been able to detect the anomalies. Finally, the candidate sets can be modified using so-called genetic algorithms until a stop criterion is validated. The genetic algorithms can, for example, consist in crossing over or mutating candidate sets.

To this end, the invention describes a method for determining a set of positions, in a fluid transport network, of a plurality of sensors of one or more physicochemical parameters of the fluid, said method comprising obtaining, for at least one set of input parameters, simulated values of physicochemical quantities at a set of points of the network for a set of time steps; obtaining a plurality of candidate sets of positions of the plurality of sensors; iteratively, until a stop criterion is validated: obtaining, for each candidate set of positions, a performance score at least from the simulated values of physicochemical quantities at the positions of the plurality of sensors; modifying the plurality of candidate sets of the sensor positions, said modification comprising at least one operation chosen from among: the retention of at least one candidate set of positions having a most favorable score; the addition of at least one candidate set of sensor positions defined by a combination of the positions of at least two candidate sets; the addition of at least one candidate set of the sensor positions defined by a modification of a position of a sensor in a candidate set; selecting the candidate set of positions having the most favorable score.

A "plurality of sets" is understood, in the present description, to mean a set of combinations of positions in the network of a given number of sensors. The optimization thus aims to determine, for a given number of sensors, the best combination to obtain the highest performance score. A plurality of combinations to be tested is defined and made to evolve on each iteration by virtue of the step of modification of the plurality of sets.

A stop criterion is a combination of rules based on the performance levels of the populations assessed in the optimization process on each iteration and of independent complementary rules:—rule based on the performance levels measured on each iteration: a certain number of successive iterations have been performed without the performance levels of the best sets, for example of the 5% of the population having the best performance levels, evolved by more than a certain percentage. A plateau is reached—a rule independent of performance levels: a maximum number of iterations set beforehand is reached. This maximum number of iterations depends on the complexity of the problem (it increases when the system to be optimized is more complex and requires more iterations).

"The most favorable score" is the value of the objective function calculated for a combination of sensor positions which provides the result that best satisfies the objectives assigned to the placement of sensors. Depending on the cases, the most favorable score is a value greater than another value of the objective function for a less favorable combination of sensor positions. For example, if the score corresponds to a number of nodes protected by the combination of sensors, the most favorable score will be the highest score, corresponding to a greater number of sensors protected. If, on the other hand, the score corresponds to a number of nodes for which an anomaly has not been detected, or has been detected too late, the most favorable score corresponds to the lowest value, and therefore to the lowest possible number of nodes for which the anomaly has not been detected. The score can be calculated on the basis of one or more elements: anomaly detection capability, number of users for which the anomalies are detected in time, equivalent consumption for which the anomalies are detected in time, rapidity with which anomalies are detected, detections of a group of anomalies having a great impact on the users, cost of deployment of the sensors, etc.

The algorithms of genetic type consist in modifying the candidate sets between two iterations, by using one or more operations chosen from among:
retention: a part of the candidates having the most favorable scores is retained, and the others are eliminated;
crossover: the positions of the sensors of at least two sets are combined. The sets between which a crossover is performed can be sets previously selected;
mutation: one or more sensor positions of a set are modified, for example randomly.

Modifying candidate sets of sensor positions, using algorithms of genetic type, in all cases allows a placement of sensors close to optimal placement to be achieved.

The method presents a relatively low algorithmic complexity (for example, the method is much less greedy than other optimization methods such as the "brute force" method which consists in testing all the options), and can be executed using common computation capacities, such as individual computers or servers, with execution times that may differ but remain reasonable. One method according to the invention, applied to a network of medium complexity, can thus be executed in a few minutes to a few hours on a personal computer, whereas a "brute force" method would take much longer to execute and even, in practice, be unable to be executed on such a computer.

The method is applicable to any type of fluid distribution network.

The method allows sensors to be placed in a network, to detect anomalies optimally at lower cost.

The method ensures a level of safety for the users of the network with a limited number of sensors.

In exemplary embodiments, the network is modelled in the form of a graph; each node or arc of the graph is identified by a unique identifier; the position of a sensor is defined by an identifier of a node or an arc of the graph.

This representation allows for a simple and effective identification of the positions of the sensors.

In exemplary embodiments, at least one of the sets of input parameters comprises the introduction of an anomaly into at least one point of the network at at least one time step.

Advantageously, this allows for a placement of sensors that optimizes the detection of anomalies in the network.

In exemplary embodiments, the performance score is calculated as a function of the capacity of the sensors placed in the candidate set of positions to detect the at least one anomaly by determining a time step of arrival of the at least one anomaly at a set of points of the network, and at least one objective function chosen from among: a number of points of the set, for which the anomaly is detected before its arrival; a number of points of the set, for which the anomaly is detected before its arrival, weighted by a number of users or a consumption per point; a number of points for which the anomaly has not been detected; a number of points for which the anomaly has not been detected, weighted by a number of users or a consumption per point.

This allows the sensors to be placed optimally, in order to prevent an anomaly that has a strong impact (for example at a reservoir) from not being detected before it affects the users of the network.

In exemplary embodiments, the performance score is calculated on the basis of at least one characteristic, chosen from among a capacity of the sensors of a candidate set to assess a quality indicator of the fluid in the network, and a cost of deployment of the sensors.

This allows the placement of sensors to be optimized, both for the detection of anomalies, and other objectives such as the traceability of the quality of the fluid throughout the subparts of the network, the protection of the sensitive sites or the limitation of the cost of deployment.

In exemplary embodiments, at least one sensor has a predefined position.

This allows the presence of pre-existing sensors to be taken into account, and the placement of additional sensors to be optimized with respect to the pre-existing sensors.

In exemplary embodiments, the points at which the sensors are placed are restricted to a subset of the points of the network.

This allows certain points of the network that do not allow the placement of sensors to be taken into account, and the placement of the sensors to be optimized with respect to the possible placement points. Site inspections can be used to select sites, on the basis of prior knowledge of the infrastructures of the network, and to invalidate some of them that exhibit excessive constraints or a prohibitive realization cost.

In exemplary embodiments, the definition of the plurality of candidate sets of positions of the plurality of sensors comprises the definition of positions at points of interest of the network.

This allows, from the first iteration, sensors to be placed at sensitive points, such as industrial sites, areas of interconnection with bulk water purchase or reservoir outlets. This allows, from the first iteration, for an efficient placement of the sensors. The method can therefore converge more rapidly to a solution close to an optimum, and requires a less great computation complexity to be executed.

In exemplary embodiments, the definition of the plurality of candidate sets of positions of the plurality of sensors comprises the definition of positions at nodes connected to a number of arcs greater than or equal to a predefined threshold.

This allows sensors to be placed only at nodes connected to a number of arcs greater than the threshold on the first iteration (for example nodes connected to at least 2, 3 or 4 arcs). These nodes are, statistically, more likely to detect the arrival of an anomaly or to protect a greater number of nodes downstream. This thus allows, from the first iteration, for an efficient placement of the sensors. The method is therefore likely to converge to a solution close to the optimum, and requires a less great computation complexity to be executed.

In exemplary embodiments, the stop criterion comprises one or more conditions chosen from among: a maximum number of iterations; a comparison of the most favorable score from among the current iteration and at least one preceding iteration, and the validation of the stop criterion if a difference between the most favorable score on the current iteration and on the at least one preceding iteration is less than or equal to a predefined threshold.

A stop criterion based on a maximum number of iterations allows for the execution time, and the computation resources required by the method, to be bounded.

A stop criterion based on a comparison between the most favorable scores between the current iteration and the preceding iterations allows the method to be stopped when the optimization gain in the placement of the sensors between at least two successive iterations becomes marginal. That allows a smaller number of iterations to be executed once the score has reached a plateau.

In exemplary embodiments, the elimination of at least one candidate set of positions not having the most favorable score comprises the elimination of all the candidate sets except for a predefined number, or a predefined ratio of the candidate sets having the most favorable score; the addition of at least one candidate set of the sensor positions defined by a combination of the positions of at least two candidate sets, and the addition of at least one candidate set of the sensor positions defined by a modification of a position of a sensor in a candidate set adding a number of candidate sets equal to the number of candidate sets eliminated.

This allows a constant number of candidate sets to be retained between the iterations, and a given number of candidate sets having the most favorable scores to be retained between two iterations. Thus, the most favorable score from among the sets on one iteration is necessarily at least equal to the most favorable score on the preceding iteration. Furthermore, this makes it possible to retain a pool of candidate sets that have good performance levels, which will also be able, through mutations or crossovers, to generate new candidates having good performance levels. This allows the method to converge more rapidly.

In exemplary embodiments, the method comprises the definition, the iterative modification, and the selection of candidate sets of sensors for a plurality of predefined numbers of sensors respectively.

This allows the performance levels of different numbers of sensors to be compared.

In exemplary embodiments, the obtaining of a plurality of candidate sets of positions of the plurality of sensors for an integer number (n) of sensors is based on the candidate set of positions having the most favorable score for an integer number (n-m) of sensors, with $1 \leq m < n$.

This allows the most efficient placement for a number (n-m) of sensors to be used as a basis for the initial placement of (n) sensors, this most efficient placement of (n-m) sensors a priori providing a good basis for an efficient placement of (n) sensors, m here being an integer lying between 1 and n.

In exemplary embodiments, the method comprises the selection of one of the candidate sets having the most favorable score for the plurality of predefined numbers of sensors, as a function of the scores and deployment costs of each of said candidate sets.

This allows the number of sensors offering the best trade-off between deployment cost and anomaly detection efficiency to be selected.

The invention also describes a method for placing a plurality of sensors of one or more physicochemical parameters of a fluid, said method comprising a determination of a set of positions in a fluid transport network, said determination comprising the steps of a method for determining a set of positions of a plurality of sensors of one or more physicochemical parameters of the fluid according to the invention, and a placement of said sensors in said set of positions.

The invention also describes a computer program product comprising program code instructions stored on a computer-readable medium comprising a processor for determining a set of positions, in a fluid transport network, of a plurality of sensors of one or more physicochemical parameters of the fluid, said computer program comprising computer-readable programming means for executing a method for determining a set of positions, in a fluid transport network, of a plurality of sensors of one or more physicochemical parameters of the fluid according to the invention.

The invention also describes a device capable of determining a set of positions, in a fluid transport network, of a plurality of sensors of one or more physicochemical parameters of the fluid, said device comprising a processor configured to execute a method for determining a set of positions, in a fluid transport network, of a plurality of sensors of one or more physicochemical parameters of the fluid according to the invention.

In exemplary embodiments, the device can be a sensor capable of calculating its optimal position and showing it through display means to a user who will position the sensor in the optimal position, by taking into account all of the sensors already deployed or currently being deployed.

BRIEF DESCRIPTION OF THE DRAWINGS

Other features will become apparent on reading the following detailed description given as a nonlimiting example in light of the attached drawings which represent:

FIGS. 7a, 7b, 7c and 7d represent four examples of placement of 2, 5, 8 and 11 sensors respectively in a water distribution network by a method for placing sensors in an embodiment of the invention for the sole purpose of detecting pollution;

FIG. 10 represents an example of water quality monitoring by sensors situated on nodes downstream of a water distribution network;

FIGS. 11a, 11b, 11c and 11d represent four examples of placement of 2, 5, 8 and 11 sensors respectively in a water distribution network by a method for placing sensors in an embodiment of the invention for the purpose of both detecting pollution and monitoring water quality downstream;

DETAILED DESCRIPTION

Hereinafter in the description, the method according to the invention is illustrated mainly by examples relating to the optimized placement of sensors for the detection of pollution and the monitoring of water quality in a potable water distribution network. However, the invention is not restricted to these examples, and can be applied to the placement of sensors for detecting other anomalies in a water network, such as leaks, and other objectives. The invention can also be applied to the optimized placement of sensors in other fluid distribution networks, such as gas distribution networks, or oil pipeline networks.

Figure 1:
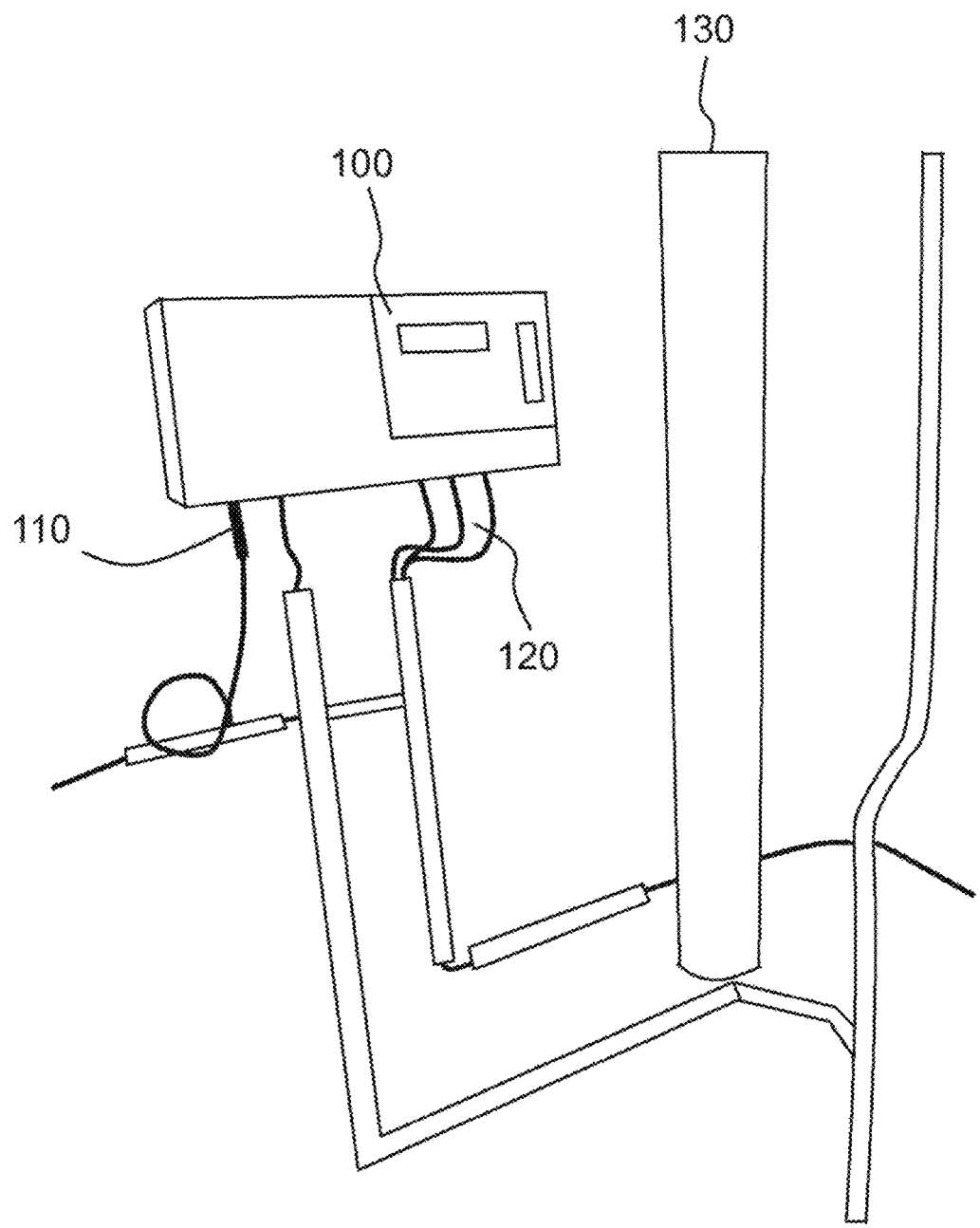
FIG. 1 represents an example of probe intended to detect anomalies in a water distribution network, that can be placed by a method according to the invention.

FIG. 1 represents an example of probe intended to detect anomalies in a water distribution network, that can be placed by a method according to the invention.

The probe 100 intended to detect anomalies in a water distribution network. The probe can be placed at any location in a water distribution network, for example at the output of a potable water production factory, at a reservoir outlet, at a consumption point, or at any other point. The applicant has filed a French patent application no 1763286 relating to a probe such as the probe 100, that allows the anomalies that occur in a water continuum to be determined.

The probe 100 is connected to pipelines 130 of the water distribution network, for example by a set of sensor cables 120, or directly connected to the network (insertion) and is powered with electricity 110 or by battery.

The probe 100 can comprise one or more sensors of physical quantities of the water distribution network. For example, the probe 100 can comprise one or more sensors chosen from among sensors of chlorine concentration, temperature, TOC (Total Organic Carbon), UV 254 (absorbance of the water for 254 nm wavelength ultraviolet light), conductivity, pH, color, turbidity, number of particles, number of bacteria, dissolved oxygen, chlorophyll a or any sensor of a physical quantity that can characterize the water.

The probe 100 thus allows, in a set of embodiments of the invention, measurements of a set of parameters representative of the quality of the water to be performed at a point of the water distribution network.

In a set of embodiments of the invention, the probe 100 comprises communication means in order to transmit the measurements of the embedded sensors. For example, the probe can comprise a wired or wireless connection to a server in order to send the measurements to a server configured to detect anomalies in the water distribution network. The probe 100 can thus be coupled to a smart water consumption sensor sending remotely read consumption data, by sending, in combination, water consumption data and sensor measurements.

In a set of embodiments of the invention, the probe comprises a processor configured to detect and characterize, from the sensor measurements, anomalies in the water distribution network.

Examples of detection and characterization of anomalies by a processor will be provided, for example, in the French patent application no 1763286.

Although the probe 100 represents an example of probe in a water distribution network, such probes can also be deployed in water in a natural environment, for example in a lake, pond, river or in any other aquatic system, and possibly at different depths.

A probe such as the probe 100 allows for the detection of anomalies such as pollutions in a water distribution network. However, these anomalies can be detected only from measurements performed by the probe. A pollution generated upstream of the probe 100 can therefore affect users, without having been detected. It is therefore important, for detecting pollutions in a water distribution network early enough to protect the users, to arrange multiple probes in the network. However, a probe such as the probe 100 has a not-inconsiderable cost of production, use and maintenance.

One objective of the invention is to provide an optimal placement of a limited number of probes in a water distribution network, in order to obtain a detection of anomalies that is as efficient as possible, and thus a good protection of the users, while retaining a reasonable economical cost. More generally, one objective of the invention is to place, in a fluid distribution network, a limited number of sensors allowing the detection of anomalies in the network, optimally in order to obtain the most efficient anomaly detection with a limited operating cost.

Figure 2:
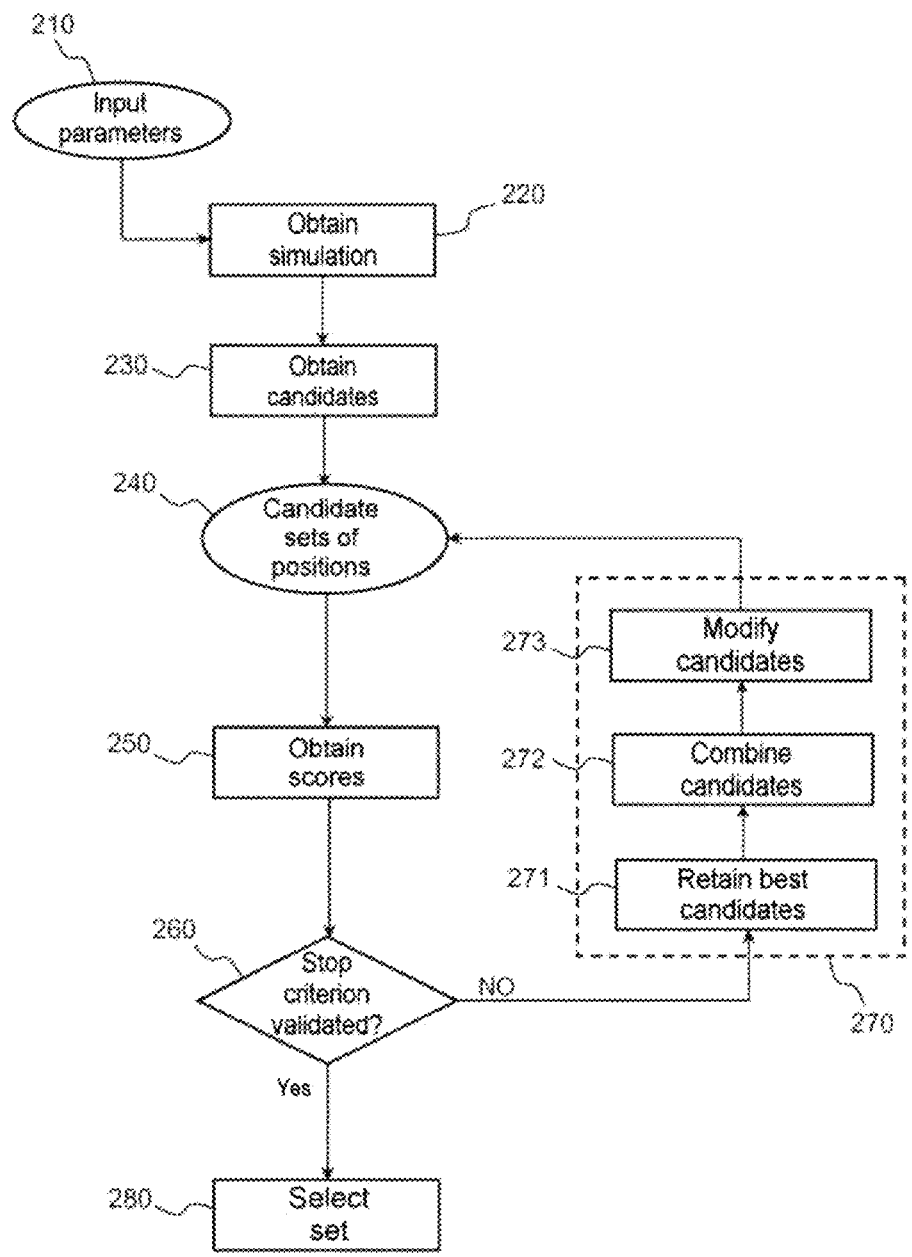
FIG. 2 represents a flow diagram of a method for placing sensors according to the invention.

FIG. 2 represents a flow diagram of a method for placing sensors according to the invention.

The method 200 is a method for determining a set of positions, in a fluid transport network, of a plurality of sensors of one or more physicochemical parameters of the fluid. The fluid distribution network can, for example, be a water or gas distribution network, or an oil pipeline network.

The method 200 is based on at least one set of input parameters 210. The input parameters allow the definition of a simulation scenario, by defining an initial state of the network, and parameters that modify the state of the network. The operation of the network can thus be simulated throughout a set of time steps. The parameters that modify the state of the network can correspond to the usual operation of the network (for example, a water consumption profile at a point of the network), or the introduction of an anomaly at a given time step. The introduction of the anomaly can be done in different ways. For example, the anomaly can be introduced at a predetermined point corresponding to a point of interest of the network (for example, the introduction of a pollution at the outlet of a factory, or at a fire hydrant). The anomalies can also be introduced, randomly, at different points of the network. The anomalies can correspond to items of variable severity, such as leaks, overpressures, or accidental or deliberate (sabotage) pollutions of the network.

The method 200 comprises the obtaining 220, for the at least one set of input parameters 210, of simulated values of physicochemical quantities at a set of points of the network for a set of time steps. Thus, the operation of the network can be simulated at different time steps, different quantities (temperature, pH, velocity, turbidity, etc.) being simulated at different points of the network for the set of time steps. The simulation can be done on each execution of the method. It can also be executed just once, for example on initialization of the method or upon the first iteration, or have been pre-computed. In this case, the simulated values simply have to be recovered to obtain the behavior of the network in a simulation scenario.

The method 200 then comprises the obtaining 230 of a plurality of candidate sets 240 of positions of the plurality of sensors. In fact, the method 200 aims to determine an optimal combination of positions of a set of sensors. As will be explained hereinbelow, the method tests different candidate sets of positions, then modifies them iteratively in order to identify the most efficient combinations, iteration after iteration.

The network, and the positions of the sensors, can be represented in different ways. For example, the network can be modelled in the form of a graph formed by nodes and arcs. The nodes can correspond to places of production or of consumption of the fluid (i.e. reservoir, grouping of consumers, factory, etc.), and the arcs can correspond to the different infrastructures allowing the fluid to be conveyed between the nodes, for example pipelines. Each node or arc can be identified by a unique identifier, the position of a sensor can then be defined by the identifier of the node or arc at which it is situated.

The obtaining 230 of the sets of sensor positions makes it possible to have sets of initial positions for the sets of sensors. These initial positions can be obtained in different ways.

For example, at least one sensor can have a predefined position. It can for example relate to sensors already arranged in the network, whose position remains fixed. Thus, the positioning of additional sensors can be optimized by taking account of the sensors already present.

The positions of the sensors can also be restricted to a subset of points of the network, for example certain nodes and/or arcs. That, for example, makes it possible to avoid placing sensors in inaccessible locations, locations for which the deployment of sensors would be too costly, locations that do not have the space necessary to arrange a sensor, or that do not allow an adequate transmission level, etc.

Among the possible placement points, the sensors can for example be initially arranged randomly. The positions can also be defined from points of interest of the network (for example factories, water holdings, etc.), these points representing good candidates for an optimal sensor placement.

The sensors can also be placed only in a subset of points corresponding to good candidates for the optimization. This allows good performance levels to be obtained, while reducing the complexity of the method. The good candidates can for example be the only points that have a high performance score according to the objective sought.

The sensors can also be placed at points of the network connected to a significant number of arcs, for example, only at nodes connected to a number of arcs greater than or equal to a predefined threshold.

These different types of initial placements can be combined. Other ways of obtaining an initial sensor placement can also be envisaged. Generally, it is desirable for the initial placement of the sensors to allow the measurements from the sensors to detect phenomena occurring in the network as efficiently as possible.

The method 200 comprises, iteratively, the obtaining of performance scores for the candidate sets of sensors, and the modification of the candidate sets using algorithms of genetic type.

The iterations then comprise the obtaining 250, for each candidate set of positions, of a performance score at least from simulated values of physicochemical quantities at the positions of the plurality of sensors. The performance score allows the point at which a set of sensor positions makes it possible to fulfill a given mission to be determined on the basis of the sensor measurements.

In a set of embodiments of the invention, the simulated values of physicochemical quantities are directly obtained for the sensor positions, and the performance score is calculated from these values.

The method 200 can also comprise an intermediate step of obtaining predictions of sensor measurements for each candidate set of positions out of said plurality for each set of input parameters. That allows, for each scenario and each candidate set, the measurements which will be performed by the sensors to be simulated. The measurements can be considered as "perfect", that is to say that the sensor measures, at each time step, precisely the value of a parameter at that time step at the position of the sensor. It is also possible to simulate the imperfections of the sensors, for example by using a sensor measurement model. Different types of models can be used, for example representing the measurement error using a Gaussian noise, the temporal granularity of the measurements using a sliding window, etc. The placement of the sensors can thus be optimized using a more realistic modelling than what is perceived by the sensors.

The obtaining of the sensor measurement predictions can thus be done by calculating the measurements, by selecting the measurements from among the simulated values of the physicochemical parameters on the network, or by recovering pre-calculated measurement predictions.

The performance score can thus be determined in different ways, depending on the objective being followed. The performance score can be calculated from an objective function representing an objective to be optimized using the suitable placement of the sensors. This objective function can for example reflect the capacity of the sensors to detect pollutions before they arrive at the users; the capacity of the sensors to detect anomalies in the network; the capacity of the sensors to assess a quality index of the fluid in the network; the cost of deployment of the sensors; a combination of multiple factors, chosen for example from among those indicated previously. Generally, the performance score can be defined so as to allow a maximum efficiency of the sensors at the lowest possible deployment cost.

At the end of the first iteration of obtaining 250 of the performance scores, the method 200 comprises a modification of the plurality of candidate sets of the sensor positions. This modification is performed through so-called genetic algorithms, that is to say through at least one operation chosen from among:
  the retention 271 of at least one candidate set of positions having a most favorable score. This so-called selection operation consists in retaining the best candidate sets, that is to say those that have obtained the best score. This makes it possible to ensure that, on each iteration, the best score out of the candidate sets will be at least as good as on the preceding iteration. Furthermore, that allows a pool of very good candidates to be retained, which will be improved as the iterations proceed. On each iteration, the candidates that are not retained are replaced by new ones, for example by the following operations;
  the addition 272 of at least one candidate set of the sensor positions defined by a combination of the positions of at least two candidate sets. This so-called crossover operation consists in combining positions derived from several candidate sets;
  the addition 273 of at least one candidate set of the sensor positions defined by a modification of a position of a sensor in a candidate set. This so-called mutation operation consists in randomly modifying the position of at least one sensor in a candidate set.

The crossovers and mutations can thus add to the set a number of candidates equal to the number of candidates not retained, in order to retain a constant number of candidates.

The different operations can be combined in different ways, generating a percentage of candidates for each iteration. In a set of embodiments of the invention, the 5% of candidates that have the best score are selected, the 80% of candidates that have an intermediate score are crossed over, and the remaining 15% are randomly mutated.

From the second score calculation iteration, that is to say after at least a first modification of the sets, the validation 260 of a stop criterion can be verified, after the calculations of the scores. This validation can be verified on each iteration, or for only certain iterations (for example one iteration in every two, one iteration in every three, etc.). The validation of the stop criterion can also be verified, only from a given number of iterations (for example from 10, 15, 20 iterations).

The stop criterion can be based on one or more conditions. For example, the stop criterion can be based on a maximum number of iterations. The stop criterion can also be based on differences between the most favorable score on the current iteration, and the most favorable score on at least one preceding iteration. In this case, the stop criterion is validated when, after one or more successive iterations, the most favorable score no longer changes, or does so only marginally.

The stop criterion can also be based on a combination of these conditions. For example, the stop criterion can be validated when a maximum number of iterations is reached and/or when the most favorable score no longer changes after one or more iterations.

As long as the stop criterion is not validated 260, new iterations of modification of the candidate sets, and score calculations are performed.

When the stop criterion is validated 260, the method 200 comprises the selection 290 of the candidate set of positions having the most favorable score.

The method 200 thus allows an optimal set of positions of the sensors to be obtained, in order to realize a desired functionality (anomaly detection, monitoring the traceability of the quality of the fluid, etc.). The method 200 offers the advantage of being able to be performed in a reasonable time with common computation capabilities, while identifying an optimal, or quasi-optimal, result.

In a set of embodiments of the invention, the method 200 can be performed for different numbers of sensors, for example several predefined numbers of sensors.

In a set of embodiments of the invention, the method is performed independently for the different numbers of sensors.

In a set of embodiments of the invention, the obtaining 230 of the candidate sets of initial positions is based at least partly on the set selected for a lower number of sensors. For example, the optimal set for a number of sensors equal to 12 to serve as a basis for an initial set of candidate sensors having 13 or 14 sensors. Indeed, it can be assumed that this optimal set, to which a few sensors would be added, can provide a good first candidate for a greater number of sensors.

It is then possible, from the best candidates for different numbers of sensors, to select the one which exhibits the best ratio between performance score and deployment cost or number of sensors.

Once the positions of the sensors are determined, their placement can be done in different ways. The invention thus also relates to a method for placing sensors at optimized positions. In a set of embodiments of the invention, the sensors are arranged at the optimized positions, for example by operators.

In a set of embodiments of the invention, the sensors have the capacity to place themselves. Such is for example the case with automatic sensor robots capable of moving around within the network. Such sensors can be located in different ways, for example using a GPS receiver, using a positioning with respect to fixed radio transmitters (positioning with respect to 3G, Wi-Fi, etc. antennas, the locations of which are known). Such robots can also be positioned with respect to a map of the network, if the robot is equipped with a topographic map of the network, and is capable of identifying the location of the network at which is located, for example using a camera. Thus, a sensor robot can, autonomously, determine its optimal position by taking account of the sensors already present, and automatically place itself there. This offers the advantage of not requiring the intervention of an operator for placing the sensors.

A set of sensor robots can also operate in network mode, by being placed automatically at the optimal positions with respect to one another. Furthermore, the sensors can then automatically, when the situation in the network changes, for example if a new sensor is added, a sensor is moved to another network, a sensor fails, etc.), recalculate their optimal positions, and move there, without needing the intervention of an operator.

Figure 3:
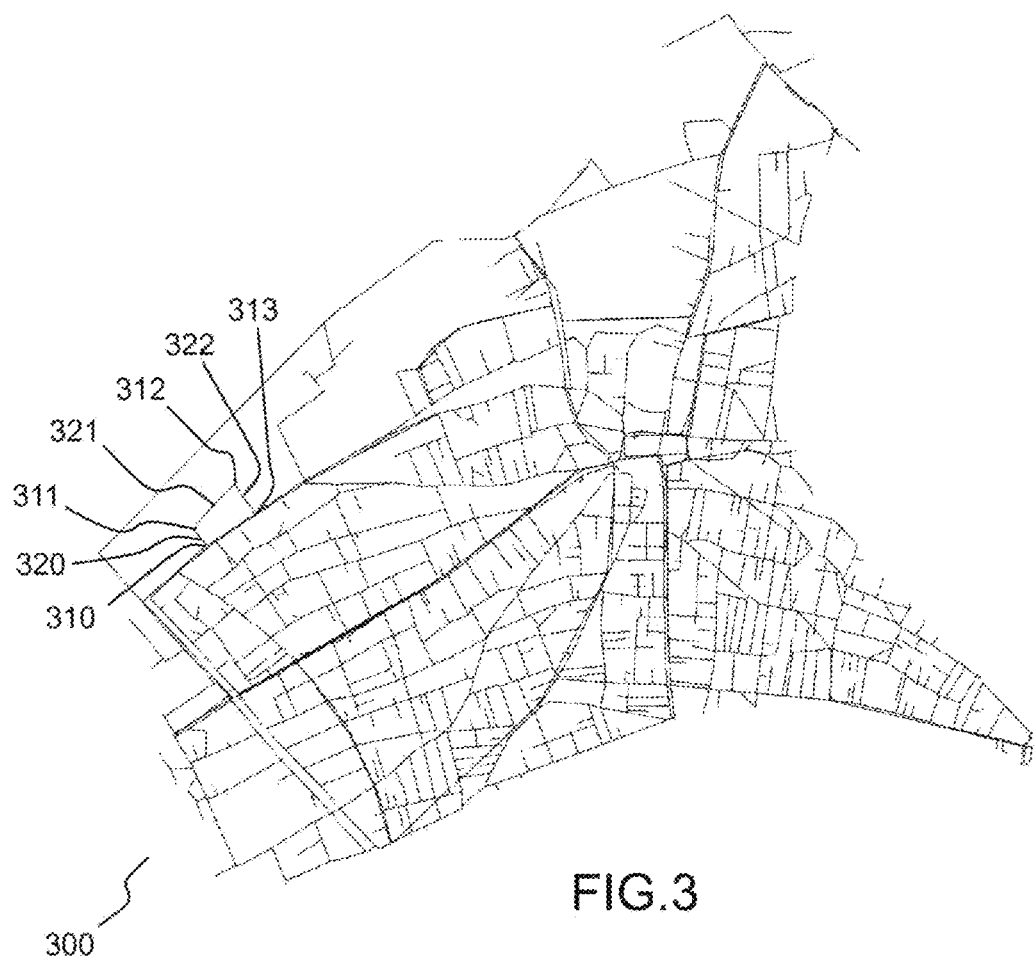
FIG. 3 represents an example of water distribution network to which the invention can be applied.

FIG. 3 represents an example of water distribution network to which the invention can be applied.

The water distribution network 300 is a town-scale network. The sector 300 is included in a large size network, numbering approximately 25000 nodes. This sector is described by a hydraulic model, represented in FIG. 3, composed of 3305 nodes, for example the nodes 310, 311, 312, 313 representing the consumption points, and 3639 arcs, for example the arcs 320, 321, 322, representing the pipelines. The nodes are connected to different numbers of pipelines. For example, the nodes 311 and 312 are connected to two pipelines, while the nodes 310 and 313 are connected to three pipelines.

It is possible to simulate the operation of a network 300 by successive time steps by using a hydraulic model. In particular, it is possible to incorporate the water consumptions (for example according to consumption profile hypotheses) at different time steps, and deduce therefrom, at each time step, the pressures at the nodes and velocities on the arcs of the network. The hydraulic model chosen can represent the median consumption profile of the network or extreme values such as the consumption peak, according to the availabilities and the wishes of the operators. It is also possible to deduce therefrom the trends of other physico-chemical parameters such as the chlorine concentration, the temperature, etc., within the network for the simulated time period.

In a set of embodiments of the invention, anomalies or pollutions can be introduced into different nodes of the network. These anomalies can represent events such as an accidental pollution or a malicious act.

Each node or arc can be represented by a unique identifier. The placement of a sensor can be performed by assigning to this sensor the unique identifier of the node or arc where it is placed.

The sector 300 is given byway of nonlimiting example only. The invention can thus be applied to many other networks, such as networks of different sizes (networks of district size, region size, etc.), or networks other than water distribution networks (oil pipelines, gas pipelines, gas distribution networks, etc.).

Hereinafter in the description, the invention will be illustrated by a use case consisting in placing sensors optimally in the network 300, with the objective of limiting the impacts caused by rapid degradations of the quality of the water. These degradations can be limited by being detected rapidly. They are called pollutions, can occur at any node of the network in different ways:

deliberate introduction of toxic substance;
backflow from a client (individual or industrial);
infiltration and works problem (refilling with water, absence of prior disinfection, particles, etc.);
significant release of biofilm because of an excessive velocity, causing an increase in bacteria and organic matter;

etc.

The pollutions do not all have the same impact depending on their position in the network and notably when they occur. The hydraulic modelling allows these aspects to be taken into account by numerically simulating the pollutions over a large number of nodes of the network. The hydraulic modelling thus allows for a mapping of the impacts caused by the different pollutions theoretically for each scenario. This mapping of the impacts makes it possible to determine the combinations of nodes best suited for sensors to be installed therein and limit or best detect these impacts. The invention thus allows the network to be covered as uniformly as possible with a limited number of sensors, by taking its hydraulic behavior into account.

In a set of embodiments of the invention, a pollution is simulated by introducing into the numerical model, at a given time step, a pollutant with a given concentration. It is also possible to introduce into the numerical model a non-reactive substance (tracer) with a dimensionless quantity concentration, for example 100. Different pollutions can be introduced at different points according to different scenarios. It is also possible to introduce anomalies other than pollutions (overpressures, bacterial growth, etc.). In this case, it is assumed that a sensor is capable of detecting a pollution above a certain tracer concentration. This is particularly effective for placing sensors such as the sensor represented in FIG. 1, which are capable of detecting many different types of pollutions.

The anomalies can be, according to different scenarios, injected at critical points, or points of interest of the network (reservoirs, factories, etc.), or even randomly. The placement of sensors can be optimized for a set of scenarios corresponding to occurrences of anomalies at different points of the network.

In a set of embodiments of the invention, anomalies are introduced at nodes randomly selected from among the nodes that have strictly more than two pipelines connected. These nodes can be called highly connected nodes, and well reflect the structure of the network by being connected to main and secondary branch lines. Introducing anomalies at nodes randomly selected from among the nodes that have strictly more than two pipelines connected makes it possible to significantly reduce the overall computation time while retaining a large number of scenarios to have an estimation of the distribution of the impacts.

The nodes at which an anomaly can be introduced can thus be randomly selected from among a list of the nodes that correspond to the chosen criterion (for example, nodes connected to strictly more than two pipelines), listed by their unique identifier, for example in the table below:

TABLE 1

Example of list of highly connected nodes of a network

| |
|---|
| 15968R |
| 21601R |
| 60328R |
| 7174R |
| 7342R |
| 15605R |
| 21390R |
| 16728R |
| 15972R |
| 27659R |
| 23776R |
| 15932R |
| 13956R |
| 20060R |

TABLE 1-continued

Example of list of highly connected nodes of a network 26854R
17958R
20012R
8530R
55822R
17444R
12261R
16070R
...

In the simulation, the pollutant introduced, or the substance constituting the numeric tracer, then spreads in the network. Progress of the substance or of the pollutant is calculated by successive time steps, via the physical equations, with or without reaction, by propagation and dilution.

In a set of embodiments of the invention, the capacity of the sensors to detect a pollution is determined using a so-called impacts matrix and a so-called detection matrix. The impacts matrix comprises a scenario per column, and a node, or point of the network, per row. It gives, for each scenario (column) and for all of the points (rows), the time step for which the pollution reaches the node in the corresponding simulation. It is constructed on the basis of transit times after which the quantities of pollutants for each node are above a predefined value, for example $10^{-6}$. This, here, is a very low threshold value for modelling the fact that pollutions, even very slight pollutions, present a risk for the users. A node is therefore touched even with an infinitesimal quantity of the tracer.

The table below presents an example of impacts matrix, in which each time step represents 10 minutes. For example, the value "36" in the cell in the first row, second column, means that, in the second scenario, the pollution reaches the node number 1 after 36×10=360 minutes (6 hours). Here, the values "144" correspond to a maximum simulation time step (24 h in this example), at which the pollution has still not reached the node.

TABLE 2

Example of impacts matrix

| 144 | 36  | 144 | 144 | 144 | 144 | 144 | 144 |
| 144 | 36  | 144 | 144 | 144 | 144 | 144 | 144 |
| 144 | 39  | 144 | 144 | 144 | 144 | 144 | 144 |
| 144 | 39  | 144 | 144 | 144 | 144 | 144 | 144 |
| 144 | 144 | 144 | 144 | 144 | 144 | 144 | 144 |
| 144 | 48  | 144 | 144 | 144 | 144 | 144 | 144 |
| 144 | 84  | 144 | 144 | 144 | 144 | 144 | 144 |
| 144 | 84  | 144 | 144 | 144 | 144 | 144 | 144 |
| 144 | 144 | 144 | 144 | 144 | 144 | 144 | 144 |
| 144 | 84  | 144 | 144 | 144 | 144 | 144 | 144 |
| 144 | 27  | 144 | 144 | 144 | 144 | 144 | 144 |
| 144 | 48  | 144 | 144 | 21  | 144 | 144 | 15  |
| 144 | 54  | 18  | 144 | 144 | 144 | 144 | 144 |
| 144 | 54  | 18  | 144 | 144 | 144 | 144 | 144 |
| 144 | 54  | 18  | 144 | 144 | 144 | 144 | 144 |
| 9   | 45  | 18  | 144 | 144 | 144 | 144 | 144 |
| 9   | 45  | 18  | 144 | 144 | 144 | 144 | 144 |
| 12  | 45  | 21  | 144 | 144 | 144 | 144 | 144 |
| 12  | 45  | 24  | 144 | 144 | 144 | 144 | 144 |
| 144 | 39  | 144 | 6   | 144 | 144 | 144 | 144 |
| 63  | 102 | 78  | 144 | 144 | 144 | 144 | 144 |
| 144 | 69  | 18  | 144 | 144 | 144 | 144 | 144 |
| 144 | 57  | 21  | 144 | 144 | 144 | 144 | 144 |
| 144 | 39  | 144 | 6   | 144 | 144 | 144 | 144 |
| 144 | 66  | 15  | 144 | 144 | 144 | 144 | 144 |

Each column of the impacts matrix is specific to each scenario, and the impacts times remain constant, regardless of the placement of the sensors. In a set of embodiments of the invention, the impacts matrix is thus calculated once for all the simulated scenarios, or has been calculated beforehand and is read from a file, in order to not have to unnecessarily recalculate the impacts of the pollution at each sensor placement. In one embodiment, once the calculation of the impacts matrix has been performed, only a subset of the scenarios of the impacts matrix is used. For example, only the columns corresponding to scenarios of pollutions having certain properties can be used: the scenarios involving the most nodes or consumption equivalents impacted, the nodes involving a percentage of nodes impacted lying between two threshold values, etc. After having simulated the scenarios, this allows only those that correspond to an impact that is sought to be minimized to be taken into account.

A detections matrix is constructed in away similar to the impacts matrix, but indicates the time step at which the pollution is detected, for a given node. In a set of embodiments of the invention, the pollution is detected when the concentration of pollutant, or of tracer, is above a predefined threshold at a node equipped with a sensor. For example, the detections matrix can comprise the time steps at which a concentration greater than or equal to 1 has been detected by a node upstream equipped with a sensor. This makes it possible to simulate the fact that the sensitivity of the sensors is limited, and that pollutions may not be detected, when the concentration of pollutant is too low, even though the pollution still has an impact.

According to different embodiments of the invention, many objective functions can be established from the comparison between the times of detection and of arrival of the pollution. For example, an objective function can consist in maximizing a number of nodes for which a pollution is detected before its arrival. Conversely, an objective function can consist in minimizing the number of points for which the pollution has not been detected. In these two cases, the number of points can be weighted by a number of users, or a consumption per point. It can also be divided by the total number of pollution scenarios or only, for each node, by the scenarios that have really impacted each of the nodes.

The comparison of the detections and impacts matrices therefore allows the lists of the nodes protected for a given set of sensor positions and for each injection scenario to be constructed. In a set of embodiments of the invention, the convention used is that a node is protected for a scenario if a sensor detects the pollution before it arrives at it. This function has the advantage of providing a trade-off between speed of detection and extent of the zone covered, since, on the one hand, the more rapidly the detection is made, the more the impact is minimized, and, on the other hand, the later and potentially more downstream in the network a detection is made, the greater the number of scenarios detected (i.e. when a pollution occurs at the center of the network, it will for example be detected by nodes downstream but not upstream in the network; conversely, a sensor situated upstream will, when it detects pollutions upstream, allow that to be done for almost all the nodes of the network). The cost of each scenario not detected is weighted by the nodes and consumptions impacted.

A node will thus be able to be considered to be protected if the detection time step for this node for a given pollution scenario is strictly less than the time step of propagation to this node. In a set of embodiments of the invention, it is not the node, but the consumption of this node, which is considered to being protected, to take account of the distribution disparities and favor the nodes with significant consumptions. The objective function used is thus the consumption not protected on average over all of the scenarios or over the set of the scenarios that in a differentiated manner impact each of the nodes, that has to be minimized.

FIG. 3 represents an example of network to which the invention can be applied, modelled in the form of a graph with nodes and arcs. However, the invention is not restricted to this example and the invention can be applied, by analogy, to other representations of a network, to optimize the capacity of the sensors to detect anomalies before they arrive at the different points of the network. For example, a 2D meshing, in which the positions of the sensors are defined by 2D coordinates (x, y) can be defined. Similarly, a 3D meshing, in which the positions of the sensors are defined by 3D coordinates (x,y,z) can be used.

Figure 4:
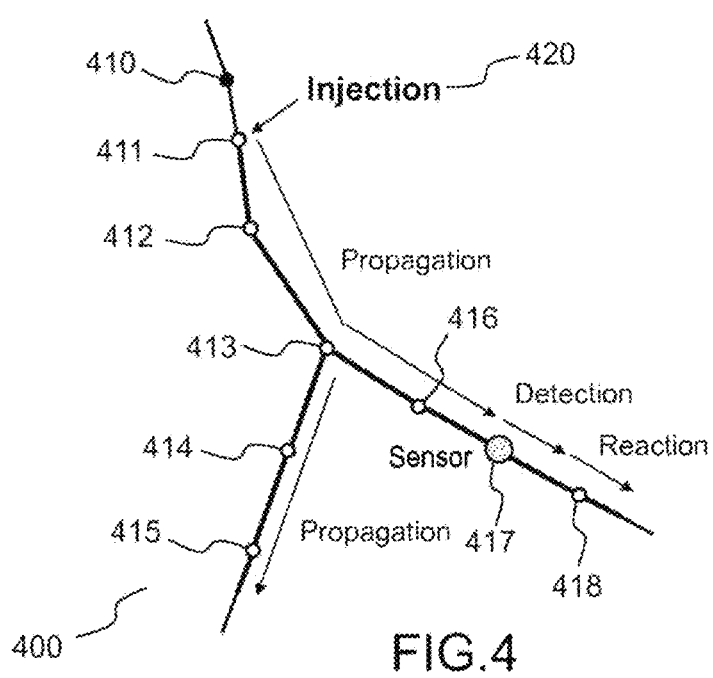
FIG. 4 represents an example of anomaly detection in a fluid distribution network according to a set of embodiments of the invention.

FIG. 4 represents an example of anomaly detection in a fluid distribution network according to a set of embodiments of the invention.

The example of FIG. 4 is based on a portion 400 of a water distribution network.

The portion 400 of network comprises nine nodes 410, 411, 412, 413, 414, 415, 416, 417, 418 linked by arcs forming three branches. The direction of flow of the water goes from the node 410 to the nodes 411, 412, 413 in succession, then from the node 413 to the nodes 414, 415, and to the nodes 416, 417, 418 respectively. This portion of network 400 is equipped with a single sensor at the node 417.

In a simulation scenario, a pollution is injected 420, at a time step, at the node 411. This pollution is propagated progressively to the nodes 412, 413, then to the nodes 414, 415 on the one hand, and 416, 417, 418 on the other hand.

Therefore, in the absence of sensor, this pollution is not detected for the nodes 411, 412, 413, 414, 415, 416. It is on the other hand detected by the sensor for the node 417. It is also detected for the node 418. It is in fact possible, as soon as the pollution is detected for the node 417, to deduce that this pollution will affect the nodes downstream such as the node 418, and deduce therefrom the appropriate corrective actions. The monitoring tools can also make it possible to analyze whether the pollution risks spreading into other zones of the network.

In a set of implementations of the invention, the performance score for a sensor placement is determined by assessing the nodes for which the pollution is detected before its arrival, and those for which the pollution is detected after its arrival, or not detected at all. This can be done for example by noting, for each node, the time step at which the pollution arrives, and the time step at which the pollution is detected, and by comparing the two. For example, impacts and detections matrices, as defined with reference to FIG. 3, can be used.

In the example of FIG. 4:
the pollution is not detected for the nodes 411, 412, 413, 414, 415, 416;
the pollution is detected after its arrival for the node 417. In fact, by its nature, at the moment when the measurements indicating a pollution are performed and processed, the pollution has already arrived at the node 417;
the pollution is detected before its arrival for the node 418. In fact, when the pollution is detected on the basis of the measurements of the sensor at the node 417, it is possible to deduce that the pollution will reach the node 418, even before its arrival, possibly with a latency time.

The placement of the sensors allows for a more or less effective detection of the pollutions. In the example of FIG. 4, a placement of the sensor at the node 412 would for example have allowed the pollution to be detected before its arrival for the nodes 413, 414, 415, 416, 417, 418.

The use of genetic algorithms for the placement of the sensors makes it possible to define, iteratively, a placement of sensors allowing for an increase in the probability of detecting an anomaly before its arrival for the highest possible number of points of the network, regardless of where the anomaly appears.

Generally, the application of genetic algorithms to the placement of sensors associated this type of anomaly detection has the effect of positioning sensors so that they detect the pollutions on average before the nodes downstream are touched: that is to say that the set of the nodes being touched by the pollution front later than the sensor will be protected. If a sensor perceives the pollution very much upstream, entire branches of the network can be protected.

Other objective functions can be used according to different embodiments of the invention. For example, the following functions can be used, alone or in combination:
the minimization of the average length of contaminated network (a pipeline is considered as contaminated if it is situated between two contaminated nodes);
the minimization of a subset of contaminated nodes from among the set of nodes (the subset can typically contain "critical" or "sensitive" nodes such as nodes corresponding to sensitive users such as hospitals, schools, etc.);
the minimization of the average pollution detection time;
the minimization of the percentage of pollution scenarios undetected. This function gives results that are fairly different from the others because the time after which the pollution is introduced and therefore its impact, are unimportant.

Figure 5:
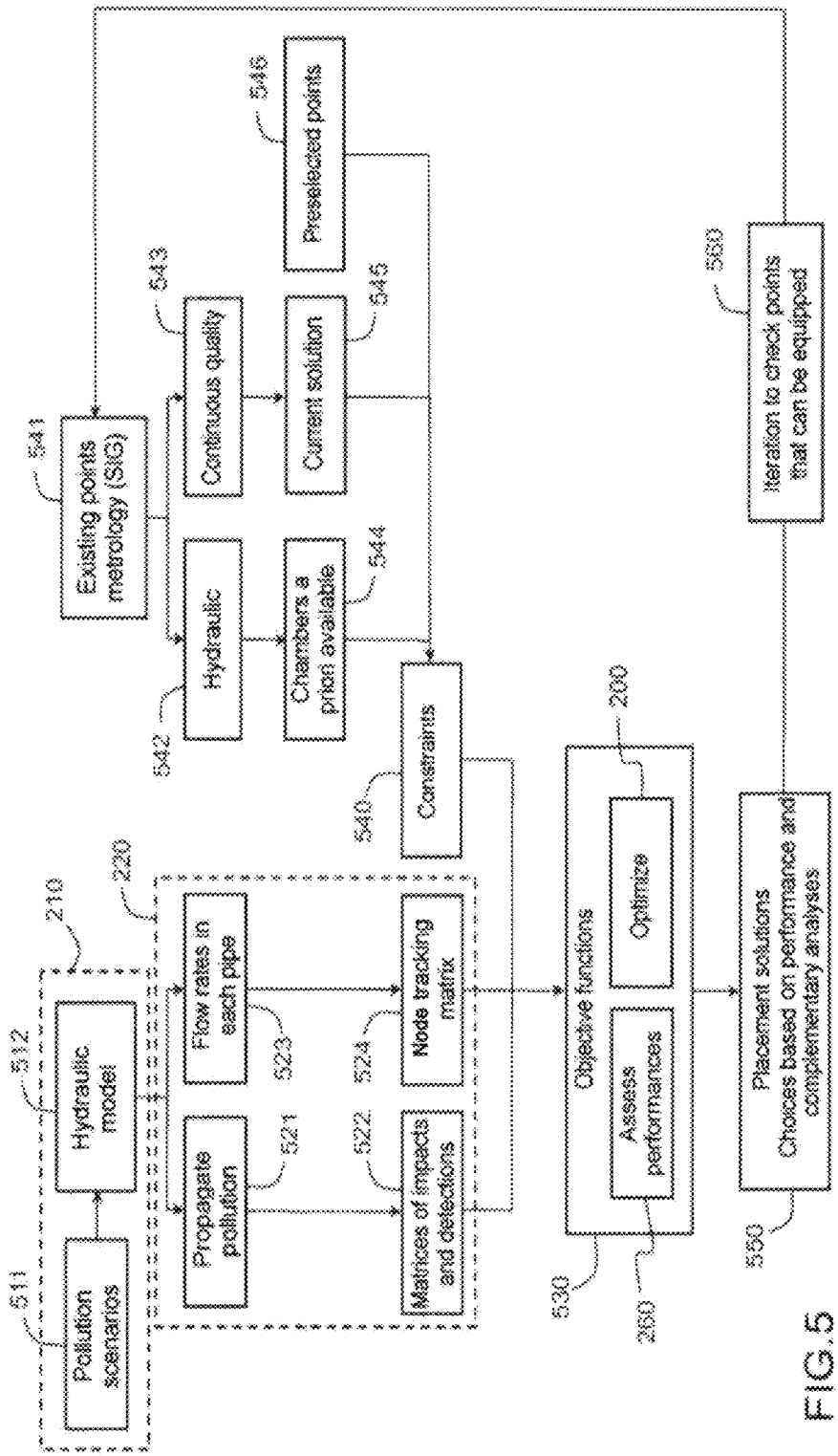
FIG. 5 represents an example of definition of optimization constraints according to a set of implementations of the invention.

FIG. 5 represents an example of definition of optimization constraints according to a set of implementations of the invention.

A method according to the invention can be parameterized according to numerous constraints and objectives. For example, input parameters 210 can be defined. These input parameters can notably comprise pollution scenarios 511, and a hydraulic model 512. These input parameters allow the operation of the network in each scenario to be simulated 220.

Notably, the input parameters 210 allow the propagation of the pollution 521 to be determined, in order to obtain a matrix of the impacts 522 representing the time of arrival of the pollution for each node. They also allow the flow rates to be determined 523 in each pipeline, in order to obtain a monitoring matrix 524 for the nodes indicating which nodes are linked to one another, and determine whether a node allows the quality of the water to be monitored in upstream nodes. The construction of such matrices is notably described with reference to FIGS. 9 and 10.

The method according to the invention can also optimize the position of the sensors, only on a subset 540 of points of the network. These points are selected from among a set of existing points 541.

The method according to the invention can incorporate equipment already provided and deployed in the network, such as:
the hydraulic sensors already deployed 542;
the quality sensors already deployed 543;

the available measurement chambers 544; the measurement chambers, already comprising sensors can be used to deploy quality sensors inexpensively;

the current solution 545, comprising the quality sensors already deployed;

the preselected nodes 546, comprising the nodes that are to be equipped, whatever they may be (sensitive sites, reservoirs, network inlets, etc.).

A method according to the invention can also be parameterized with one or more objective functions 530 indicating the objective monitored by the placement of the sensors. These objective functions allow performance scores to be calculated 250 upon the execution 200 of the method for placing sensors according to the invention.

The optimal placement solution obtained can thus be analyzed 550 by an operator, to check that it is satisfactory. In the case where this solution should be suboptimal, for example if a placement point has not been retained because it did not form part of the subset of points authorized for the optimization, this problem can be detected by the operator, who can thus check the sensor placement constraints, and modify them if necessary 560, before proceeding with a new placement iteration.

Figure 6:
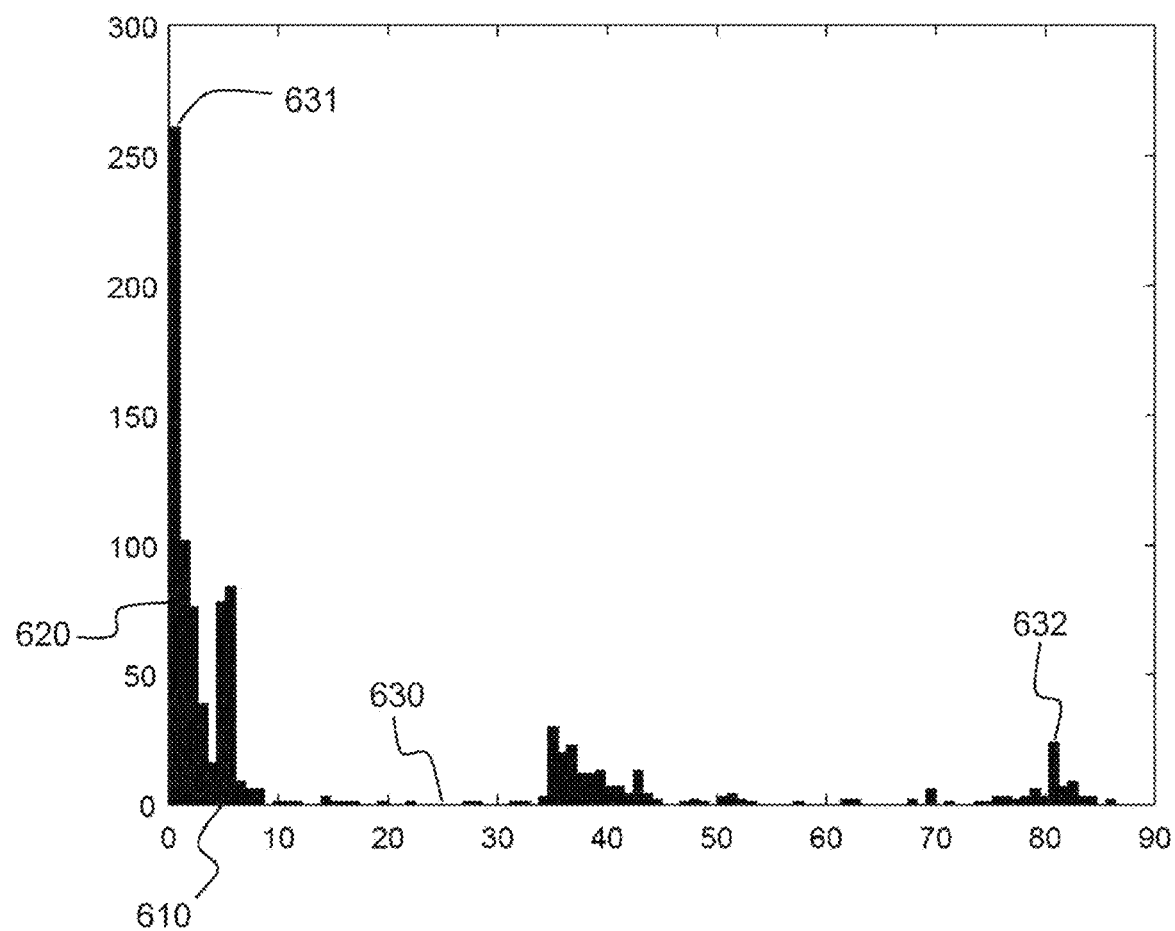
FIG. 6 represents an example of histogram of different test scenarios for the placement of sensors with their percentages of nodes of a water distribution network affected by each pollution.

FIG. 6 represents an example of histogram representing the percentages of nodes of a water distribution network impacted by a pollution according to 940 test scenarios for the placement of sensors on the sector 300.

FIG. 6 represents:

on the x axis 610, the percentages of nodes touched for the different scenarios;

on the y axis 620, the number of scenarios corresponding to each percentage of nodes impacted.

FIG. 6 thus shows that the percentage of nodes impacted by the pollutions is highly variable depending on the scenarios: in more than 250 scenarios, between 0 and 1% of the nodes are impacted 632, whereas, in 20 or so scenarios, more than 80% of the nodes are impacted, and an almost zero number of scenarios impacts between 20 and 30% of the nodes 630.

FIGS. 7a, 7b, 7c and 7d represent four examples of placement of 2, 5, 8 and 11 sensors respectively in a water distribution network by a method for placing sensors in an embodiment of the invention targeting only the pollution detection.

In this example, a method for optimizing placement of sensors according to the invention has been executed with the following parameters.

The nodes on which the sensors were able to be placed in this example satisfied various criteria:

they are connected to strictly more than two arcs;

they have a minimum scenario detection of 5. This can be achieved, by determining, for each scenario, the nodes at which the pollution can be detected. It is then possible, conversely, to determine, for each node, the number of pollution scenarios that it will be capable of detecting, and to preselect the nodes which are capable of detecting the pollution for a number of scenarios greater than a predefined threshold, for example 5;

the nodes on which a sensor is already deployed, or unfavorable to the deployment of a sensor (field constraint requiring an excessively high investment, constraints on any roadworks, heavy traffic, etc.) are eliminated.

Limiting the optimization of certain nodes allows the nodes where the placement of a sensor is impossible to be eliminated and/or the problem and execution of the method according to the invention to be simplified, while basing the optimization on the nodes that are a priori the most favorable. However, these constraints are given purely by way of nonlimiting example, and other constraints can be used. For example, the minimum scenario detection number can depend on the number of sensors to be tested, in order to be adapted to the complexity of the problem.

The optimization is then performed, in succession for a number of sensors ranging from 1 to 20.

The plurality of candidate sets of positions is initially obtained, by randomly selecting the sensors from among the preselected nodes, then several optimization iterations by genetic algorithm are performed.

On each iteration, a score is calculated for each candidate set, as a function of a percentage of the consumption not covered by the sensor measurements (i.e. the nodes for which a pollution is not detected are identified, weighted by their relative consumption and related to the total number of nodes, to obtain a percentage of the consumption for which a pollution has not been detected. The lower this percentage is, the better the candidate set is).

The genetic algorithm is then applied to modify the plurality of candidate sets on each iteration, as a function of the scores, according to the following rules:

the best 5% of candidate sets are retained (selection of the elites);

80% of intermediate candidate sets are crossed over with one another, and/or with the "elites" (best candidates) to generate new sets;

the 15% of candidate sets that have obtained the least good scores mutate, that is to say they are randomly modified.

This application of the method 200 according to the invention allows an optimal placement to be obtained for each number of sensors. Once the method is performed for a number N of sensors, the optimal solution using N sensors is used as a basis for optimizing N+1 sensors.

An optimal placement is thus obtained for each of the numbers of sensors between 1 and 20.

These examples show that, generally, the method according to the invention produces a relatively uniform placement of the sensors on the network, thus allowing anomalies occurring at any point to be detected. One advantage of the invention is retaining, upon the addition of a sensor, the positions of the sensors previously placed, only if this position remains optimal. That is the case in FIGS. 7a to 7d:

the two sensors 710a, 720a are retained when the number of sensors increases 710b, 720b, 710c, 720c, 710d, 720d;

the additional three sensors 730c, 740b, 750b of the solution with 5 sensors are retained when the number of sensors changes to 8 (730c, 740c, 750c) or 11 (730d, 740d, 750d).

However, contrary to other algorithms such as the "greedy" algorithms, in the invention, if the addition of a new sensor makes the position of the sensors previously placed non-optimal, this position will be modified.

Figure 8:
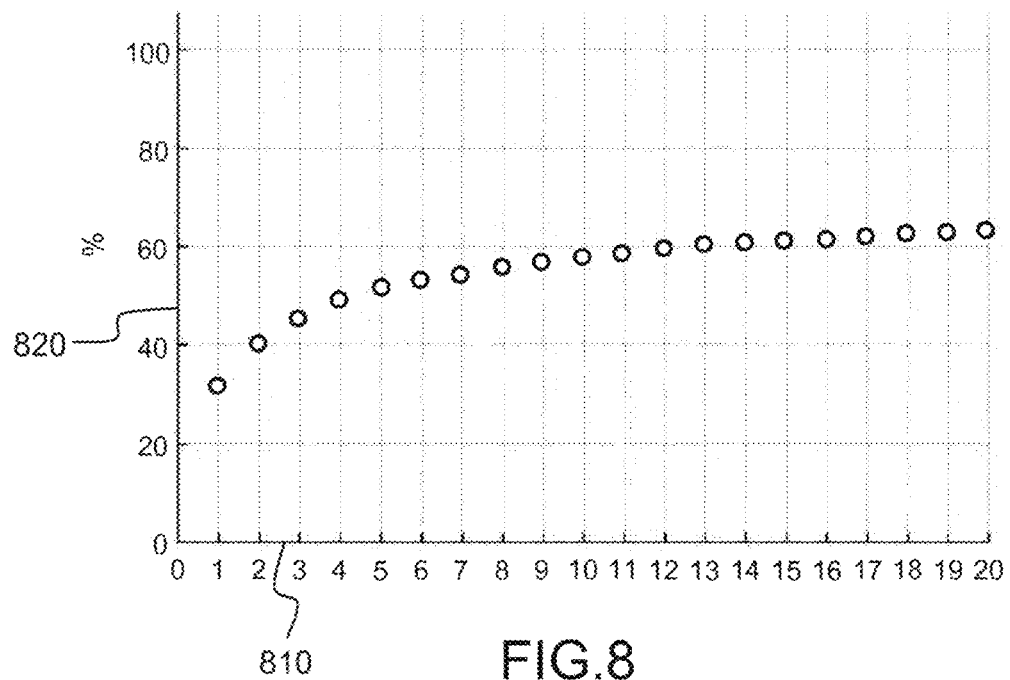
FIG. 8 represents the trend of a percentage anomaly detection by sensors in a water distribution network placed by a method according to the invention, as a function of the number of sensors.

FIG. 8 represents the trend of a percentage of detection of anomalies by sensors in a water distribution network placed by a method according to the invention, as a function of the number of sensors.

The x axis 810 represents the number of sensors placed, between 1 and 20, in the example previously described. The y axis 820 represents the percentage of nodes considered as covered, that is to say the percentage of nodes for which a pollution is detected before its arrival.

FIG. 8 shows that the increase in the number of sensors initially allows for significant protection gains. The marginal protection gain associated with the addition of a new sensor becomes less and less significant as the number of sensors deployed increases. The invention thus allows an optimal number of sensors to be chosen, either as a function of a target coverage rate, or as a function of a percentage optimization of coverage/deployment cost.

The optimizations presented with reference to the FIGS. 7a to 7d, and 8 are given purely by way of nonlimiting example. The invention is not restricted to these examples, and the method according to the invention can optimize the placement of sensors according to many different constraints.

For example, in some sectors, the optimization can be done only on a subset of the points, in order to best make use of the existing infrastructures.

Sectors that have reservoirs of large sizes can be optimized by introducing a measurement point downstream of the reservoirs in order to monitor the pollutions which could specifically touch them. These points are considered as fixed and included in the populations of combinations of sensors tested. They have the effect of detecting pollutions at the reservoirs. If the reservoirs are not used as points of intrusion in the scenarios tested, the input from these points in the performance levels is zero.

A sector which includes a hospital can generate the additional constraint of equipping the entry point of the latter, which is in fact one of the consumption nodes of the hydraulic model. This is taken into account for the optimization as forcing of the solution. The point of the hospital is thus present in the set of combinations assessed in the optimization process. It contributes to the detection performance levels by detecting the pollution scenarios situated upstream of the hospital and that can touch other points.

Another sector with several sensitive installations (i.e. military, industrial and other such installations) can be optimized by weighting the nodes of the model corresponding to these sites, in order for them to be prioritized in the optimization process. The objective function thus allows the sensors to be placed by favoring the protection of the sensitive sites against the pollutions, even by protecting only those by weighting them at 1 and all the others at 0.

The fact of being able to choose to optimize the network as a whole, or in a differentiated manner according to the sectors, thus allows more flexibility and adaptation to the field constraints and to the expertise of the potable water distribution professionals. The optimization by sectors of all the sectors thus makes it possible to reduce the computation times compared to global optimization.

The method according to the invention can thus be adapted to very different operational contexts, and allows an optimal sensor placement, for very different objectives. The method according to the invention can be configured by the user, based on his or her knowledge of the networks to which it is applied.

Figure 9:
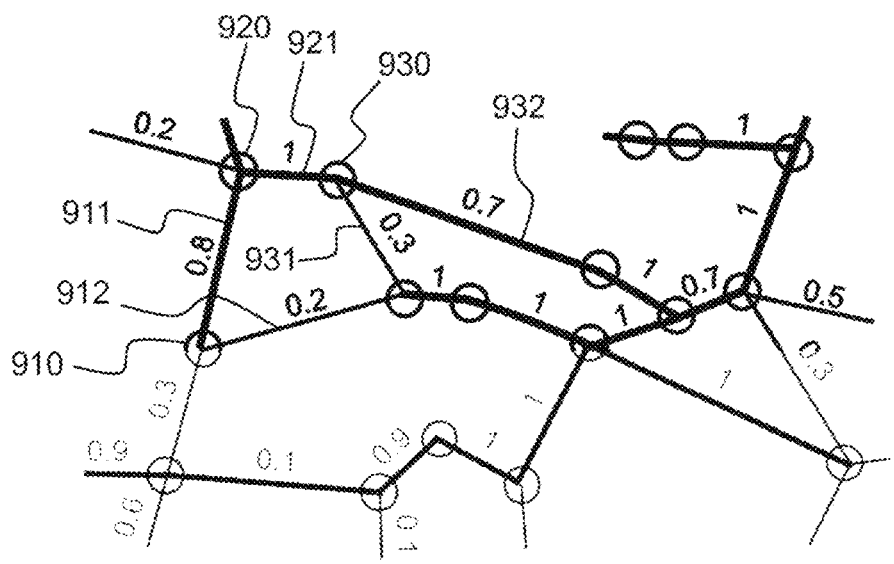
FIG. 9 represents an example of distribution of the flow rates in a water distribution network.

FIG. 9 represents an example of distribution of the flow rates in a water distribution network.

A method according to the invention can be used to optimize the placement of sensors for the detection of anomalies or of pollution. It can also be used for other purposes, such as optimizing water quality monitoring. To this end, the score assigned to each candidate set of sensor positions can be calculated on the basis of a function consisting in determining the number of nodes through which the water has transited at the time of measurement. This type of monitoring, called downstream monitoring, can rely on the generation of a flow rate fractioning matrix. For the set of nodes, the percentages of flow rate transiting in each of the adjacent pipelines downstream is calculated at different time steps.

FIG. 9 provides an example of flow rate fractioning. FIG. 9 indicates the directions of flow of the water, and the fractions of flow rate going in each pipeline. The flow in the network is generally, in this example, from left to right. The numbers indicated on each pipeline indicate the fraction of the flow rate which goes from one node to another. For example:

for one unit, the flow rate entering at the node 910 is fractioned at 0.8 (80%) in the pipeline 911, and at 0.2 (20%) in the pipeline 912;

for one unit, the flow rate entering at the node 920 is fractioned at 1 (100%) in the pipeline 921;

for one unit, the flow rate entering at the node 930 is fractioned at 0.3 (30%) in the pipeline 931, and at 0.7 (70%) in the pipeline 932.

This relationship at the directly adjacent nodes is then propagated throughout the network. In a set of embodiments of the invention, a downstream monitoring relationship is defined for a pair of nodes if one of the two receives a majority fraction of the flow rate having transited through the other (>50%). The links represented in bold show the nodes considered to be linked to one another. For example, the node 910 is considered to be linked to the node 920, and the node 920 to the place 930. If the threshold of 50% of flow rate provides a good indication of the link between two nodes, other thresholds (40%, 60%, etc.) can also be used.

It is thus possible, for each of the nodes of the graph, to determine the number of upstream nodes to which it is linked, that is to say the number of nodes through which the water received will have transited. The nodes can also be assigned to the population, or associated consumption. Thus, it is possible to deduce, for each node, what population, or water consumption, will be covered by a quality monitoring performed at this node.

FIG. 10 represents an example of monitoring of the quality of the water by sensors situated on nodes downstream of a water distribution network.

FIG. 10 shows how the nodes surrounded by rhomboids are considered to be tracked by the nodes surrounded by a star. The flows are symbolically represented, highlighting at this time step the structure and the hydraulic behavior of the network.

FIG. 10 represents the sector 300, of which the portion 1000 is represented enlarged below the image. In the example of FIG. 10, the nodes have been linked iteratively, when more than 50% of the flow rate entering into a node transits to the next node. For example, the node 1011 is linked to the node 1012, which is itself linked to the node 1013, etc., up to the node 1010. The node 1011 is therefore linked 1014 to the node 1010. FIG. 10 represents all the nodes linked to another with a rhomboid, and the links between the nodes by thick grey lines, such as the line 1014. FIG. 10 shows that a large part of the nodes of the network converge either to the downstream node 1010, or to the downstream node 1020. This representation therefore allows for a better understanding of the structure of the flow rates and of the hydraulic behavior of the network, at a given time step.

Sensors placed at nodes 1010 and 1020 thus allow the quality of the water to be checked over a large part of the network.

A method according to the invention allows sensors to be placed to optimally monitor the quality of the water, by calculating the performance score using an objective function defining the number of nodes to which a node is linked, that is to say a number of nodes for which a node can perform downstream monitoring. Such an objective function allows the sensors to be placed so as to be able to monitor different water qualities originating from different sources and above all from different zones of mixing of these sources. Generally, the sensors placed using this objective function can also detect pollutions occurring downstream of the network.

This objective function can be used on its own, or in combination with an objective function concerning anomaly or pollution detection. The presence of sensors for downstream monitoring can thus complement the sensors placed with the objective function of pollution detection. This combination is also well-suited to the subdividing of the network into water sub-lots corresponding to a source or a mix of sources.

FIGS. 11a, 11b, 11c and 11d represent four examples of placement of 2, 5, 8 and 11 sensors respectively in a water distribution network by a method for placing sensors in an embodiment of the invention targeting both pollution detection and water quality monitoring.

The placement of the sensors is performed on the same principle as for the example of FIGS. 7a to 7d, except for the following points.

As indicated above, in order to simplify the problem while obtaining good performance levels, the sensors can be placed only in a subset of the nodes of the network. As explained with reference to FIGS. 9 and 10, the nodes that allow an optimal placement of the sensors for the downstream monitoring of the pollution are the nodes linked to a large number of nodes of the network situated upstream. The subset of the nodes on which the placement of sensors is possible can therefore comprise the nodes that are connected, according to the rule defined with reference to FIG. 9, to a number of nodes upstream greater than or equal to a predefined threshold. The consumption per node can also be considered, and the subset of nodes on which the optimization is performed can comprise the nodes that are connected to a number of nodes upstream corresponding to a consumption greater than a predefined threshold.

To optimize the placement of sensors jointly for anomaly detection and downstream monitoring, it is relevant to preselect nodes that form good candidates for anomaly detection, and nodes that form good candidates for downstream water quality monitoring. For example, the subset of nodes on which the optimization is performed can comprise nodes that are connected to a large number of nodes upstream (forming good candidates for downstream monitoring), and nodes that are connected to a number of arcs greater than a predefined threshold (forming good candidates for anomaly detection).

During the optimization, the score assigned to each of the candidate sets of positions is calculated on the basis of a combined objective function, equal to the average of an objective anomaly detection function and of an objective water quality monitoring function, in order to favor the candidate sets of positions that allow both good anomaly detection and good water quality monitoring.

The genetic algorithm is then applied to modify the plurality of candidate sets on each iteration, as a function of the scores, according to the following rules:
 the best 5% of candidate sets are retained (selection of the elites);
 the 80% of intermediate candidate sets are crossed over with one another and/or the "elite" nodes (best candidates retained) to generate new sets;
 the 15% of candidate sets that have obtained the least good scores mutate, that is to say that they are randomly modified.

This application of the method 200 according to the invention allows an optimal placement to be obtained for each number of sensors. Once the method has been performed for a number N of sensors, the optimal solution using N sensors is used as a basis for the optimization of N+1 sensors.

An optimal placement is thus obtained for each of the numbers of sensors between 1 and 20.

The placements of the nodes are represented, for 2, 5, 8 and 11 respectively, by circles such as the circle 1110a. For a same number of sensors, the placement is, here, different from that performed for FIGS. 7a to 7d. For example, in the solution with 5 sensors, the sensor 1120b is placed in a zone where no sensor was situated in FIG. 7b (solution with 5 sensors for pollution detection only). This sensor 1120b allows water quality monitoring over all the north part of the network, and has therefore allowed the solution with 5 sensors presented in FIG. 11b to obtain a good score for the "anomaly detection+water quality monitoring" combination.

These examples demonstrate the capacity of the invention to provide an optimal sensor placement as a function of an objective defined by the user. The invention is therefore applicable to a large number of use cases, and allows an optimal placement of sensors to be obtained according to a large number of different criteria.

Figure 12:
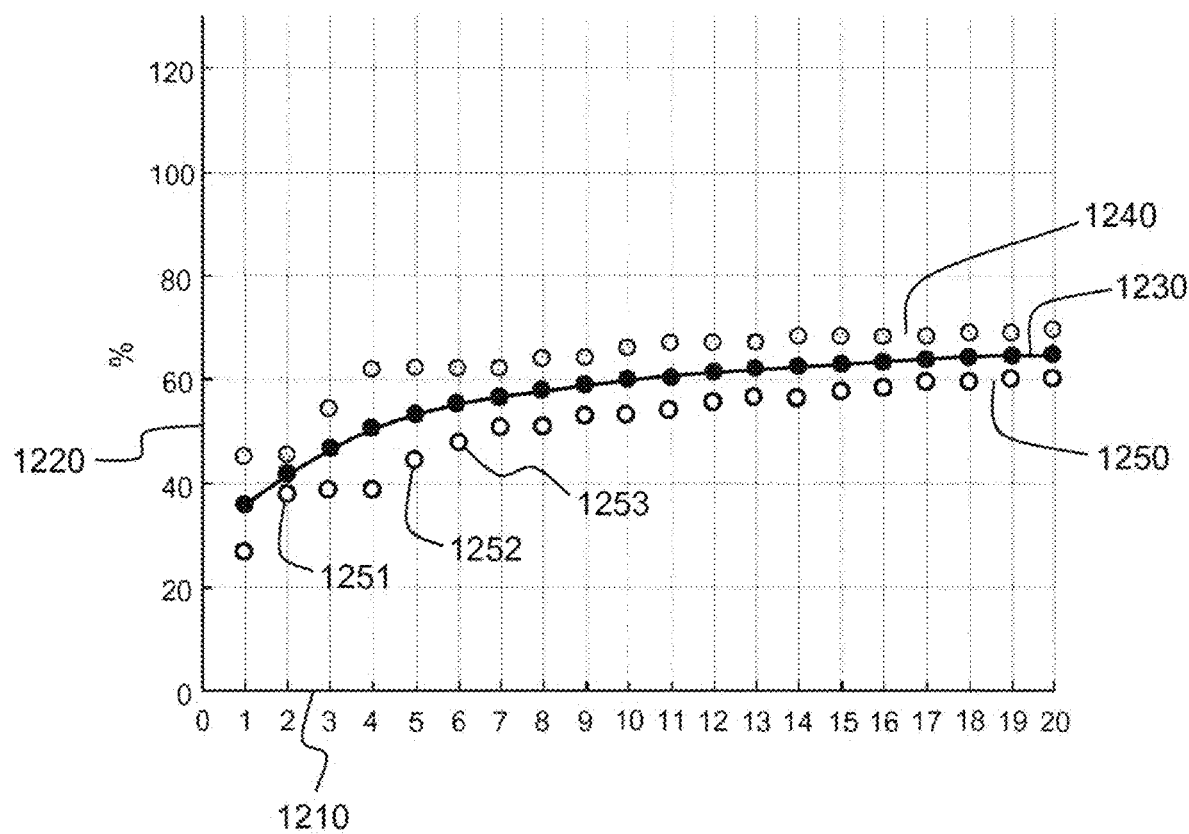
FIG. 12 represents the trend of a combined pollution detection and water quality monitoring score as a function of a number of sensors placed by a method according to the invention.

FIG. 12 represents the trend of a combined pollution detection and water quality monitoring score as a function of a number of sensors placed by a method according to the invention.

The curves of FIG. 12 are created on the same principle as the curve of FIG. 8: the x axis 1210 represents the number of sensors placed, and the vertical axis 1220 represents the performance score of the optimal solution, expressed as a percentage, and the curve 1230 the trend of the score as a function of the number of sensors, in the example of FIGS. 11a to 11d.

As indicated above, in the combined optimization example of FIGS. 11a to 11d, the performance score is calculated as the average of a water quality monitoring score and of an anomaly detection score. The top curve 1240 represents the water quality monitoring score and the bottom curve 1250 represents the anomaly detection score. When a new sensor is added, the overall score can be increased by increasing the water quality monitoring score and/or the anomaly detection score. For example, the additions of the third and fourth sensors have, here, primarily improved the water quality monitoring score 1241, 1242, whereas the additions of the second, fifth and sixth sensors have primarily improved the anomaly detection score 1251, 1252, 1253.

This example demonstrates the capacity of the invention to arrange the sensors optimally according to a combination of objectives, by improving one or other of the objectives to obtain the best overall score.

The examples above demonstrate the capacity of the invention to optimize the placement of sensors according to different target criteria. They are however given purely by way of example and do not in any way limit the scope of the invention, defined in the claims below.

The invention claimed is:

1. A method for determining a set of positions, in a fluid transport network, of a plurality of sensors of one or more physicochemical parameters of a fluid, said method comprising:

obtaining with a processor, for at least one set of input parameters, simulated values of physicochemical quantities at a set of points of the fluid transport network for a set of time steps;

obtaining with the processor a plurality of candidate sets of positions of the plurality of sensors;

iteratively performing with the processor, until a stop criterion is validated, at least the following processes:

i. obtaining with the processor, for each candidate set of positions, a performance score at least from the simulated values of physicochemical quantities at the positions of the plurality of sensors;

ii. modifying with the processor the plurality of candidate sets of sensor positions, said modification comprising at least one operation chosen from among:

iii. conservation with the processor of at least one candidate set of positions having a most favorable score;

iv. addition with the processor of at least one candidate set of sensor positions defined by a combination of the positions of at least two candidate sets; and v. addition of at least one candidate set of sensor positions defined by a modification of a position of a sensor in a candidate set;

selecting with the processor the candidate set of positions having the most favorable score; and providing the candidate set of positions to a user for an optimal placement of a given number of sensors in the fluid transport network.

2. The method as claimed in claim 1, wherein:
the fluid transport network is modelled in graph form;
each node or arc of the graph is identified by a unique identifier; and
a position of a sensor is defined by an identifier of a node or arc of the graph.

3. The method as claimed in claim 2, wherein a definition of the plurality of candidate sets of positions of the plurality of sensors comprises the definition of positions at nodes connected to a number of arcs greater than or equal to a predefined threshold.

4. The method as claimed in claim 1, wherein at least one of the sets of input parameters comprises introduction of an anomaly in at least one point of the network during at least one time step.

5. The method as claimed in claim 4, wherein the performance score is calculated as a function of a capacity of the sensors placed in the candidate set of positions to detect the at least one anomaly by determining a time step of arrival of the at least one anomaly at a set of points of the fluid transport network, and at least one objective function chosen from among:

a number of points of the set, for which the anomaly is detected before its arrival;

a number of points of the set, for which the anomaly is detected before its arrival, weighted by a number of users or a consumption per point;

a number of points for which the anomaly has not been detected; and a number of points for which the anomaly has not been detected, weighted by a number of users or a consumption per point.

6. The method as claimed in claim 1, wherein the performance score is calculated from at least one characteristic, chosen from among a capacity of the sensors of a candidate set to assess a quality indicator of the fluid in the fluid transport network, and a cost of deployment of the sensors.

7. The method as claimed in claim 1, wherein at least one sensor has a predefined position.

8. The method as claimed in claim 1, wherein the points at which the sensors are placed are restricted to a subset of the points of the fluid transport network.

9. The method as claimed in claim 1, wherein a definition of the plurality of candidate sets of positions of the plurality of sensors comprises the definition of positions at points of interest of the fluid transport network.

10. The method as claimed in claim 1, wherein the stop criterion comprises one or more conditions chosen from among:

a maximum number of iterations; and/or a comparison of the most favorable score out of a current iteration and at least one preceding iteration, and the validation of the stop criterion if a difference between the most favorable score at the current iteration and at the at least one preceding iteration is less than or equal to a predefined threshold.

11. The method as claimed in claim 1, wherein:

an elimination of at least one candidate set of positions not having the most favorable score comprises the elimination of all the candidate sets except a predefined number, or a predefined ratio of the candidate sets having the most favorable score; and the addition of at least one candidate set of the sensor positions defined by a combination of the positions of at least two candidate sets, and the addition of at least one candidate set of the sensor positions defined by a modification of a position of a sensor in a candidate set add a number of candidate sets equal to the number of candidate sets eliminated.

12. The method as claimed in claim 1, comprising a definition, an iterative modification, and the selection of candidate sets of sensors for a plurality of predefined numbers of sensors respectively.

13. The method as claimed in claim 12, wherein the obtaining of a plurality of candidate sets of positions of the plurality of sensors for an integer number (n) of sensors is based on the candidate set of positions having the most favorable score for an integer number (n–m) of sensors, with $1 \leq m < n$.

14. The method as claimed in claim 12, comprising the selection of one of the candidate sets having the most favorable score for the plurality of predefined numbers of sensors, as a function of the scores and costs of deployment of each of said candidate sets.

15. A method for placing a plurality of sensors of one or more physicochemical parameters of a fluid, said method comprising:

a determination of a set of positions in a fluid transport network, said determination comprising the steps of a method as claimed in claim 1, and a placement of said sensors in said set of positions.

16. A non-transitory computer readable medium containing computer instructions stored therein for causing a computer processor to perform steps of the method as claimed in claim 1.

17. A device capable of determining a set of positions, in a fluid transport network, of a plurality of sensors of one or more physicochemical parameters of the fluid, said device comprising a processor configured to execute the method as claimed in claim 1.

* * * * *